United States Patent
Peltola et al.

(10) Patent No.: US 10,825,251 B2
(45) Date of Patent: *Nov. 3, 2020

(54) SYSTEMS AND METHODS FOR PROVIDING MEDICAL INFORMATION AND FOR PERFORMING A MEDICALLY-RELATED PROCESS USING AUGMENTED REALITY TECHNOLOGY

(71) Applicant: Varian Medical Systems International AG, Cham (CH)

(72) Inventors: Jarkko Peltola, Tuusula (FI); Mikko Juhani Vainio, Espoo (FI); Janne I. Nord, Espoo (FI); Santtu Tuomo Tapani Ollila, Helsinki (FI); Anri Maarita Friman, Espoo (FI); Ronan MacLaverty, Helsinki (FI)

(73) Assignee: Varian Medical Systems International AG (CH)

( * ) Notice: Subject to any disclaimer, the term of this patent is extended or adjusted under 35 U.S.C. 154(b) by 25 days.

This patent is subject to a terminal disclaimer.

(21) Appl. No.: 15/892,157

(22) Filed: Feb. 8, 2018

(65) Prior Publication Data

US 2019/0243138 A1    Aug. 8, 2019

(51) Int. Cl.
| | |
|---|---|
| *G06T 19/00* | (2011.01) |
| *G02B 27/01* | (2006.01) |
| *G16H 30/20* | (2018.01) |
| *G16H 10/60* | (2018.01) |
| *G06T 17/10* | (2006.01) |

(52) U.S. Cl.
CPC ........ *G06T 19/006* (2013.01); *G02B 27/0103* (2013.01); *G02B 27/0172* (2013.01); *G06T 17/10* (2013.01); *G16H 10/60* (2018.01); *G16H 30/20* (2018.01); *G02B 27/017* (2013.01); *G02B 2027/0138* (2013.01)

(58) Field of Classification Search
CPC .. A61N 5/1039; A61N 5/1038; G02B 27/017; G02B 2027/0138; G06F 3/0482
See application file for complete search history.

(56) References Cited

U.S. PATENT DOCUMENTS

| | | | |
|---|---|---|---|
| 5,329,567 A * | 7/1994 | Ikebe | A61B 6/0457 378/195 |
| 6,888,919 B2 | 5/2005 | Graf | |
| 7,649,981 B2 | 1/2010 | Seppi et al. | |

(Continued)

OTHER PUBLICATIONS

Talbot, James, "A Patient Position Guidance System in Radiotherapy Using Augmented Reality", https://pdfs.semanticscholar.org/83df/68db1967d9e0420f3ed1f651c3a9df6ce48c.pdf, Jun. 15, 2016. (Year: 2016).*

(Continued)

*Primary Examiner* — Michelle L Sams
(74) *Attorney, Agent, or Firm* — Vista IP Law Group, LLP

(57) ABSTRACT

An apparatus for use in a medical process that involves a particle accelerator, includes: a processing unit configured to obtain medical information, obtain a viewing direction of a user of the apparatus, and process the medical information based on the viewing direction of the user of the apparatus to create a graphical representation of the medical information for presentation to the user of the apparatus; and a screen for displaying the graphical representation.

42 Claims, 10 Drawing Sheets

(56) References Cited

U.S. PATENT DOCUMENTS

| | | | |
|---|---|---|---|
| 2008/0081982 A1* | 4/2008 | Simon | G06F 19/3481 |
| | | | 600/407 |
| 2014/0022283 A1* | 1/2014 | Chan | G02B 27/017 |
| | | | 345/633 |
| 2015/0306340 A1 | 10/2015 | Giap et al. | |
| 2016/0331997 A1 | 11/2016 | Vilsmeier | |
| 2017/0039423 A1* | 2/2017 | Cork | G06K 9/00671 |
| 2017/0165501 A1 | 6/2017 | Rapaka et al. | |
| 2017/0252108 A1* | 9/2017 | Rios | G06F 19/00 |
| 2018/0063386 A1 | 3/2018 | Sharma et al. | |

OTHER PUBLICATIONS

Karp, Joel S. PhD, "Time-of-Flight PET", http://snmmi.files.cms-plus.com/docs/PETCENews_Fall06.pdf, Fall 2006. (Year: 2006).*

Wikipedia, "See-through display", https://web.archive.org/web/20170105101449/https://en.wikipedia.org/wiki/See-through_display, Jan. 5, 2017 (Year: 2017).*

Rodas, Nicolas Roy, "Context-aware radiation protection for hybrid operating room", Feb. 2018, https://www.researchgate.net/publication/324963779 (Year: 2018).*

Non-Final Office Action dated Jun. 7, 2019 for related U.S. Appl. No. 15/892,226.

Jain, N. "Augmented Reality on Mobile Devices: Advancing Globally Accessible Anatomical Education", (2013), Retrieved from http://www.nishantjain.com/medical-virtual-reality.html.

Final Office Action dated Nov. 4, 2019 for related U.S. Appl. No. 15/892,226.

Non-Final Office Action dated Mar. 10, 2020 for related U.S. Appl. No. 15/892,226.

* cited by examiner

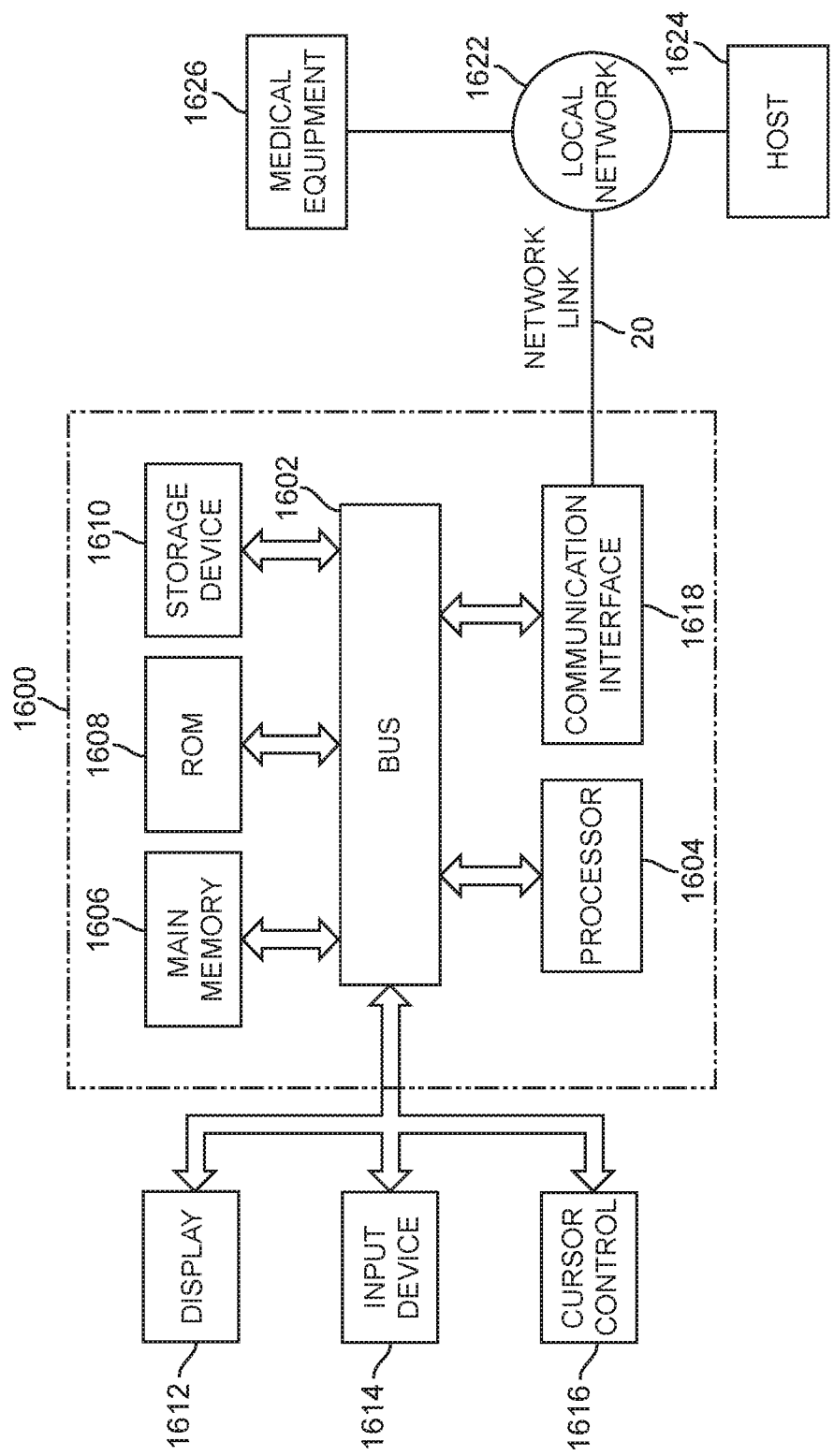

SYSTEMS AND METHODS FOR PROVIDING MEDICAL INFORMATION AND FOR PERFORMING A MEDICALLY-RELATED PROCESS USING AUGMENTED REALITY TECHNOLOGY

FIELD

The field of the application relates to medical devices, and more particularly, to medical devices for providing medical information and for performing a medically-related process using augmented reality technology.

BACKGROUND

Radiation therapy involves medical procedures that selectively deliver high doses of radiation to certain areas inside a human body. Also, particle (e.g., electron, proton, etc.) beam treatment may be used to provide certain treatments. In either radiation therapy or particle beam treatment, the patient is first positioned next to the treatment machine, and a patient setup procedure is performed to align the patient with the treatment machine. After the patient has been set up, the technician then operates the treatment machine to deliver treatment energy towards the patient. Currently, the control for controlling the treatment machine is located in a separate control room that is away from the treatment room where the treatment machine is located. So during or after a treatment procedure, the technician may view various information related to the treatment in a screen located in the control room. New devices and methods for presenting medical information to technician are described herein.

SUMMARY

In accordance with one specific implementation of an embodiment, an apparatus includes a wearable augmented reality device, such as virtual reality glasses or a holographic visor. The apparatus is configured for sensing the three-dimensional (3D) shape of the surrounding space, tracking the position of the device in that space, and projecting images in the field of view of the user in real-time, to assist in collision detection after patient setup. The apparatus is worn by the operator who is positioning the patient in the treatment room. The apparatus builds a 3D model of the patient volume during the setup of patient while the patient is supported on a patient support. The apparatus then simulates and/or monitors the treatment-time movements of the treatment unit and the patient (with couch) and alerts for collisions between the two. Additionally, positions where the treatment unit comes to close proximity of the patient can be readily detected in the holographic projection by the operator (and algorithmically), which allows the patient to be advised of such situations in order to alleviate patient's concerns regarding collision with the treatment machine.

In accordance with another specific implementation of an embodiment, an apparatus includes a wearable augmented reality device, such as virtual reality glasses or a holographic visor. The apparatus is configured for sensing the three-dimensional (3D) shape of the surrounding space, tracking the position of the device in that space, and projecting images in the field of view of the user in real-time, to assist in patient positioning. The apparatus is worn by the operator who is positioning the patient in the treatment room. The apparatus builds a 3D model of the patient during the patient setup on the support device. The apparatus then projects the 3D CT/MRI image of the patient as used in treatment planning onto the translucent glass/visor surface within the operator's field of view. Other visual cues include, but are not limited to, the position of the isocenter, calculated dose, the treatment fields, and relevant organs, such as bones and the target(s), or any combination thereof, on or inside the actual patient as seen by the operator. The expected positions of patient anatomical features can be projected as well. The apparatus provides visual cues that help the operator to align the patient with the expected position and the treatment machine in all six degrees of freedom, which reduces inter-fraction variance of dose distribution due to patient position.

In accordance with another specific implementation of an embodiment, an apparatus includes a wearable augmented reality (AR) device, such as virtual reality glasses or a holographic visor. The apparatus is configured for projecting three-dimensional images in the field of view of the user in real-time, to assist in patient identification using multiple methods. The apparatus is worn by the operator who calls/assists the patient in to the treatment room, and/or who is responsible for patient setup for treatment. The apparatus projects the patient identification photograph for side-by-side visual comparison. Additionally, biometric identification algorithms, such as face, iris, hand, ear, and voice recognition, can be used to verify patient identity based on data collected via the sensors of the AR device. The data collection can take place during transition from waiting/changing room to the treatment room or inside the treatment room. The apparatus can support the use of bar codes, QR codes, or other visual tagging technologies, or hand-held radio frequency identification device (RFID) readers, for patient identification. The identification methods can be configurable in order to adapt to the identification practices specific to the clinic. The apparatus can automatically identify the patient using multiple methods simultaneously, and prompt for approval or additional verification as needed.

In accordance with another specific implementation of an embodiment, an apparatus includes a wearable augmented reality device, such as virtual reality glasses or a holographic visor. The apparatus is configured for being used in the treatment for in situ emergency planning directly on a patient CBCT and fast dose calculation, resulting in better treatment with less side effects. The apparatus utilizes augmented reality to allow real-time positioning of the patient and treatment beams, while the patient is stationary in the treatment room. The augmented reality provided by the apparatus allows the treater to see the planned dose delivery directly on the patient. The treater can then shape the dose and try different treatment configurations. In these cases, carefully contoured structure sets are not available to a treater when making their plans, but can be inferred directly from the patient. Overlaying the dose on the patient would clarify impact of the treatment on the patient. In cases where there are no CT images available for dose calculation, the depth of the treatment isocenter can be rendered on to the patient by the apparatus, so the treater can estimate the impact of the MUs planned, and can adjust the plan if necessary. In some cases, augmented reality can be used to create a volumetric patient model from patient surface. The patient surface is scanned from the top of the patient support device and the approximate patient model is filled with water electron density matter. This gives an approximation of both the patient shape and the electron densities within the patient. Accordingly, the apparatus can calculate the approximate 3D dose distribution in certain depth in treatment isocenter. In the cases where TOF and multiple cameras are not available, the headset of the apparatus can be used to capture the patient's physique in a similar manner to TOF technologies. Using augmented reality, the apparatus can provide the quality of the model to the user, who can continue to take additional sample points until the model closely relates to the patient. Additionally, in some cases, the apparatus may be configured to modify this model to match the patient's anatomy (e.g., through deformation transformation). In cases where CT/CBCT images are available, these can be rendered by the apparatus in a cross section on the patient, located at the treatment isocenter, and orthogonal to the treater. Calculated dose can be rendered by the apparatus on the cross section, thus allowing the treater to view the dose delivery's effects on the patient's organs. There are several ways of rendering image information, such as: (1) Render images within the patient along the axes of the isocenter lasers, so that the treater can position the patient correctly, (2) Render images within the patient orthogonal to the treater's headset (e.g., by moving the user's head wearing the apparatus to "scan" the patient, a 3-D model of the patient's internal structure can be estimated). In cases where images are not available, the estimated dose can be rendered in the same way.

In accordance with another specific implementation of an embodiment, an apparatus includes a wearable augmented reality device, such as virtual reality glasses or a holographic visor. The apparatus is configured for being used in the treatment room for assisting a user to adjust the patient to match a treatment plan, and/or for assisting the user to determine a treatment plan. The apparatus is advantageous over the approach in which the treatment console and imaging guidance system are in a separate room different from the treatment room in which the patient is located. The apparatus makes it easier for the user to adjust the patient to match the treatment plan, without constantly going back and forth between the treatment room to position the patient, and the treatment console to check the positioning. The apparatus is also advantageous over the approach in which treatment target information is provided on an iPad. This is because the apparatus may be configured to provide the same treatment target information, but in an overlay configuration directly over the patient as viewed through the screen of the apparatus, so that the treatment target appears "inside" the patient's body. Also, in some embodiments in which the apparatus is configured for worn at the user's head, the user may use his/her hands to manipulate the patient, without having to hold the iPad. Thus, the apparatus is an improvement in the technology of patient setup, treatment planning, and treatment execution.

In some cases, the apparatus may provide treatment information (e.g., planned/accumulated dose, differences in targets and organs shapes and sizes, isocenter locations) for display on the screen of the apparatus, so that the user of the apparatus can adapt the treatment plan while the patient is in the treatment room. Also, in some cases, isocenter lasers may be extrapolated within the patient's body (i.e., as viewed by the user of the apparatus) to help the user of the apparatus align the patient with the treatment target. Augmented reality provided by the apparatus adds value, because the patient will be simultaneously visible as the apparatus renders one or more useful features over the patient's body as viewed through the screen of the apparatus. Augmented reality provided by the apparatus may also allow the user of the apparatus to view the patient's treatment location from different angles, beam information, and other relevant patient treatment information.

Also, in some cases, the apparatus may display information to inform the user of changes to the patient's posture, and/or changes to the patient's anatomy. Such information may assist the user in adjusting the patient to adapt a treatment plan and/or to determine a new treatment plan based on the existing condition of the patient. In one implementation, one or more modalities may be used to provide detailed information about the patient's internal and/or external structure(s), and such information may be displayed on the screen of the apparatus. In some embodiments, images of structures used for treatment planning may be displayed together with the current images of the same structures at the screen of the apparatus. This allows changes of structures to be easily observed, and can help guide adaptation of the treatment plan.

In some cases, for treatment plan adaptation, the apparatus may provide dose variations overlayed on the patient's tumor and critical organs, so that the user of the apparatus may adjust the patient for the treatment plan. For example, if a patient's hand is incorrectly placed, this may impact a treatment beam, leading to an incorrect dose delivery. Also, in some cases, the apparatus may provide a preview of beam angles and positions for display on the screen, so that the user of the apparatus may readily see how the beams will traverse different parts of the patient. For example, if the user sees that a preview of a beam undesirably traverses a patient's hand, the user may then adjust the patient's posture accordingly. In further cases, the apparatus may provide other guidance information for assisting the user of the apparatus to alter a setup to allow treatment to occur. For example, changes to the patient's anatomy (for example, due to weight loss) would also be evident by comparing planning structure sets with the physical reality of the patient. In some embodiments, the apparatus may allow the user to determine a new treatment plan by selecting one of a plurality of pre-determined treatment plans, or by changing a parameter of a current treatment plan.

In other embodiments, instead of providing the various information on the screen of the apparatus that is for worn at the user's head, the same information may be projected onto the patient using one or more projectors inside the treatment room. In further embodiments, virtual reality technology may be used to instruct the patient to alter his/her setup (e.g., position, posture, etc.) remotely.

An apparatus for use in a medical process that involves a particle accelerator, includes: a processing unit configured to obtain medical information, obtain a viewing direction of a user of the apparatus, and process the medical information based on the viewing direction of the user of the apparatus to create a graphical representation of the medical information for presentation to the user of the apparatus; and a screen for displaying the graphical representation.

Optionally, the apparatus further includes a wearable device, wherein the screen is a part of the wearable device.

Optionally, the apparatus further includes an orientation sensor coupled to the wearable device, wherein the processing unit is configured to vary the graphical representation based on an input from the orientation sensor.

Optionally, the apparatus further includes a positioning device coupled to the wearable device, wherein the processing unit is configured to vary the graphical representation based on an input from the positioning device.

Optionally, the wearable device comprises a virtual-reality device.

Optionally, the screen comprises a transparent screen for allowing the user to see surrounding space.

Optionally, the screen is a part of a handheld device.

Optionally, the graphical representation has a variable configuration that corresponds with the viewing direction of the user.

Optionally, the processing unit is also configured to obtain patient information regarding a geometry of a patient, wherein the processing unit is configured to process the medical information based on the patient information and the viewing direction of the user of the apparatus.

Optionally, the apparatus further includes a time-of-flight camera for providing distance information, wherein the patient information comprises a surface of the patient that is based on the distance information.

Optionally, the patient information comprises a digital image of the patient, a digital image of another person different from the patient, or a model of an artificial patient.

Optionally, the medical information comprises planned dose, delivered dose, image of internal tissue of a patient, target shape, target position, critical organ shape, critical organ position, or any combination of the foregoing.

Optionally, the medical information comprises dose information, and wherein the processing unit is configured to create the graphical representation of the dose information based on the viewing direction of the user, and to provide the graphical representation for display over a patient or for display in an overlay configuration with an image of the patient.

Optionally, the medical information comprises tissue geometry, and wherein the processing unit is configured to create the graphical representation of the tissue geometry based on the viewing direction of the user, and to provide the graphical representation for display over a patient or for display in an overlay configuration with an image of the patient.

Optionally, the processing unit is configured to create the graphical representation along isocenter axes as viewed by the user.

Optionally, the processing unit is also configured to provide a user interface for allowing the user to determine a treatment parameter for a treatment plan while a patient is supported on a patient support.

Optionally, the processing unit is also configured to obtain patient information, the patient information comprising an image of a patient, the medical information comprising dose information, and wherein the processing unit is configured to obtain the medical information by calculating the dose information based on the image of the patient.

Optionally, the image of the patient comprises a CT image.

Optionally, the processing unit is also configured to obtain a patient model created based on a detected surface of the patient, wherein the processing unit is configured to process the medical information based on the patient model and the viewing direction of the user of the apparatus to create the graphical representation.

Optionally, the patient model comprises a volumetric model approximating a shape of the patient and densities within the patient.

Optionally, the medical information comprises dose information, and wherein the processing unit is configured to determine the dose information based on the patient model.

Optionally, the medical information comprises a depth of a treatment isocenter, and the processing unit is also configured to render the depth of the treatment isocenter over a patient or for display in an overlay configuration with an image of the patient.

Optionally, the processing unit is also configured to obtain patient information, the patient information comprising a position of a patient, and wherein the medical information comprises image data of the patient; and wherein the processing unit is configured to create the graphical representation of the image data based on the viewing direction of the user and the position of the patient.

Optionally, the graphical representation comprises a cross section of a CT image.

Optionally, the medical information further comprises dose information, and the graphical representation illustrates the dose information on the cross section of the CT image.

Optionally, the processing unit is configured to create the cross section of the CT image along isocenter axes.

Optionally, the processing unit is configured to create the cross section of the CT image along a direction that is orthogonal to the viewing direction of the user.

Optionally, the screen comprises a transparent portion for allowing the user to view a real world.

Optionally, the screen is a part of a holographic device configured to project three-dimensional images in a field of view of the user in real-time.

Optionally, the processing unit is also configured to provide a photograph of a patient for display on the screen.

Optionally, the apparatus further includes a sensor configured to sense a characteristic of a patient for biometric identification.

Optionally, the characteristic comprises a facial feature, an iris feature, a retina feature, a hand feature, an ear feature, a fingerprint, or a voice.

Optionally, the processing unit is configured to compare the sensed characteristic with a pre-determined characteristic of the patient.

Optionally, the apparatus further includes a sensor configured to sense an identification of a patient, wherein the screen is configured to display the identification of the patient.

Optionally, the identification comprises a barcode, a quick-response (QR) code, or a RFID.

Optionally, the processing unit is further configured to obtain room information, and to generate positional information based on the room information for assisting the user to position a patient, and wherein the processing unit is configured to provide the positional information for display on the screen.

Optionally, the room information comprises a position of an object in a room, the object being a component of a machine, a patient support, a wall, a floor, a ceiling, or an alignment device.

Optionally, the medical information comprises an expected position of a patient, and wherein the processing unit is configured to provide the graphical representation of the expected position of the patient for display on the screen.

Optionally, the screen is configured to display the graphical representation of the expected position of the patient in a field of view of the user while the user is viewing the patient in real-time.

Optionally, the apparatus further includes a user interface for allowing the user to position the patient based on the graphical representation of the expected position of the patient.

Optionally, the apparatus further includes a sensor for sensing an object next to a patient, wherein the processing unit is configured to generate a signal for notifying the user in response to the sensed object being within a certain distance from a surface of the patient.

Optionally, the medical information comprises a safety zone that is above a surface of the patient.

Optionally, the sensor comprises a surface detector.

Optionally, the medical information comprises an image of the patient.

Optionally, the processing unit is also configured to obtain object information regarding an object involved in the medical process, and provide the object information for display on the screen to assist in validation of the object.

Optionally, the object comprises a treatment machine, a patient support, a fixation device for fixing a portion of a patient in place, a bolus, a medication, or an accessory.

A method performed by an apparatus in a medical process that involves a particle accelerator, comprising: obtaining, by a processing unit of the apparatus, medical information; obtaining, by the processing unit of the apparatus, a viewing direction of a user of the apparatus; processing, by the processing unit of the apparatus, the medical information based on the viewing direction of the user of the apparatus to create a graphical representation of the medical information for presentation to the user; and displaying the graphical representation in a screen of the apparatus.

An apparatus for use in a medical process that involves a particle accelerator, includes: a processing unit configured to obtain treatment plan information, obtain a viewing direction of a user of the apparatus, and process the treatment plan information based on the viewing direction of the user of the apparatus to create a graphical representation of the treatment plan information for presentation to the user of the apparatus; and a screen for displaying the graphical representation.

Optionally, the treatment plan information comprises a position of an energy source for delivering a treatment beam.

Optionally, the graphical representation comprises a line representing a trajectory of the treatment beam.

Optionally, the treatment plan information comprises an expected configuration of a component of a treatment machine.

Optionally, the expected configuration comprises an expected position of the component of the treatment machine.

Optionally, the treatment plan information comprises an expected dose for an internal target of a patient.

Optionally, the graphical representation indicates the expected dose graphically, and wherein the processing unit is configured to provide the graphical representation for display over a patient as viewed through the display, or for display in an overlay configuration with an image of the patient, so that the graphical representation is at a location that corresponds with a position of the internal target of the patient.

Optionally, the treatment plan information comprises an expected posture of a patient.

Optionally, the treatment plan information comprises a target position, a target size, a target shape, a critical organ position, a critical organ size, a critical organ shape, or any combination of the foregoing.

Optionally, the treatment plan information comprises a target fluence, and the processing unit is configured to provide the graphical representation for representing the target fluence.

Optionally, the treatment plan information comprises a trajectory of a component of a treatment machine, and wherein the graphical representation is configured to indicate the trajectory of the component of the treatment machine.

Optionally, the processing unit is configured to simulate a treatment based on the treatment plan information, and wherein the graphical representation comprises one or more images represented the simulated treatment.

Optionally, the one or more images comprises a sequence of images forming a video.

Optionally, each of the images in the video is based on a viewing direction and position of the user of the apparatus.

Optionally, the simulated treatment comprises a simulated movement of a component of a treatment machine.

Optionally, the graphical representation comprises a video showing the simulated movement of the component of the treatment machine.

Optionally, the apparatus further includes a user interface for allowing the user to determine a new treatment plan by selecting the new treatment plan from a plurality of pre-determined treatment plans, while a patient is supported on a patient support.

Optionally, the apparatus further includes a user interface for allowing the user to determine a new treatment plan by changing a parameter of a current treatment plan, while a patient is supported on a patient support.

Optionally, the apparatus further includes a wearable device, wherein the screen is a part of the wearable device.

Optionally, the apparatus further includes an orientation sensor coupled to the wearable device, wherein the processing unit is configured to vary the graphical representation based on an input from the orientation sensor.

Optionally, the apparatus further includes a positioning device coupled to the wearable device, wherein the processing unit is configured to vary the graphical representation based on an input from the positioning device.

Optionally, the wearable device comprises a virtual-reality device.

Optionally, the screen comprises a transparent screen for allowing the user to see surrounding space.

Optionally, the screen is a part of a handheld device.

Optionally, the graphical representation has a variable configuration that corresponds with the viewing direction of the user.

Optionally, the apparatus further includes a camera unit coupled to the processing unit.

Optionally, the camera unit comprises an optical camera, a depth camera, or both the optical camera and the depth camera.

Optionally, the processing unit is configured to provide the graphical representation for display over a patient as viewed through the display, or for display in an overlay configuration with an image of the patient.

Optionally, the processing unit is also configured to determine an image of a patient, and output the image of the patient for display on the screen based on the viewing direction of the user of the apparatus.

Optionally, the image comprises a CT image, a x-ray image, a MRI image, an ultrasound image, a tomosynthesis image, an on-line image, or a dose image.

Optionally, the processing unit is configured to determine a treatment dose, and output a graphic representing the treatment dose for display on the screen based on the viewing direction of the user of the apparatus.

Optionally, the apparatus further includes a user interface for allowing the user to control a position of an energy source, a patient support, one or more camera(s), one or more alignment laser(s), one or more light(s), a calibration of a device, a speaker for communication with a patient, music for presentation to the patient, or any combination of the foregoing.

Optionally, the processing unit is configured to receive a real-time consultation from a person who is different from the user of the apparatus, and provide guidance information for display on the screen for assisting the user to determine and/or to adapt a treatment plan.

Optionally, the processing unit is configured to obtain multiple positions of an isocenter at different respective times, and provide a graphic indicating change(s) of the isocenter over time for display on the screen.

Optionally, the processing unit is configured to obtain multiple values of dose at different respective times, and provide a graphic indicating how the dose varies over time.

Optionally, the processing unit is configured to provide patient setup information for display on the screen, the patient setup information indicating weight change and/or positional change, of a patient.

Optionally, the processing unit is configured to provide information regarding fluence virtualization for display on the screen.

Optionally, the apparatus further includes a database configured to store data documenting one or more activities that occur in a treatment room.

Optionally, the data represents a treatment setup configuration, a patient setup configuration, a patient behavior, or any combination of the foregoing.

Optionally, the data indicates how a treatment was executed.

Optionally, the data indicates positions of a component of a treatment machine at different respective times, and/or a timing of energy delivery.

Optionally, the screen comprises a transparent portion for allowing the user to view a real world.

Optionally, the screen is a part of a holographic device configured to project three-dimensional images in a field of view of the user in real-time.

Optionally, the treatment plan information comprises a simulated dose effect on a target region and/or critical organ.

Optionally, the processing unit is configured to simulate an execution of a treatment plan to determine the simulated dose effect on the target region and/or critical organ.

A method performed by an apparatus in a medical process that involves a particle accelerator, includes: obtaining, by a processing unit of the apparatus, treatment plan information; obtaining, by the processing unit of the apparatus, a viewing direction of a user of the apparatus; processing, by the processing unit of the apparatus, the treatment plan information based on the viewing direction of the user of the apparatus to create a graphical representation of the treatment plan information for presentation to the user; and displaying the graphical representation in a screen of the apparatus.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 9 illustrates a specialized processing system.

DETAILED DESCRIPTION

Figure 1:
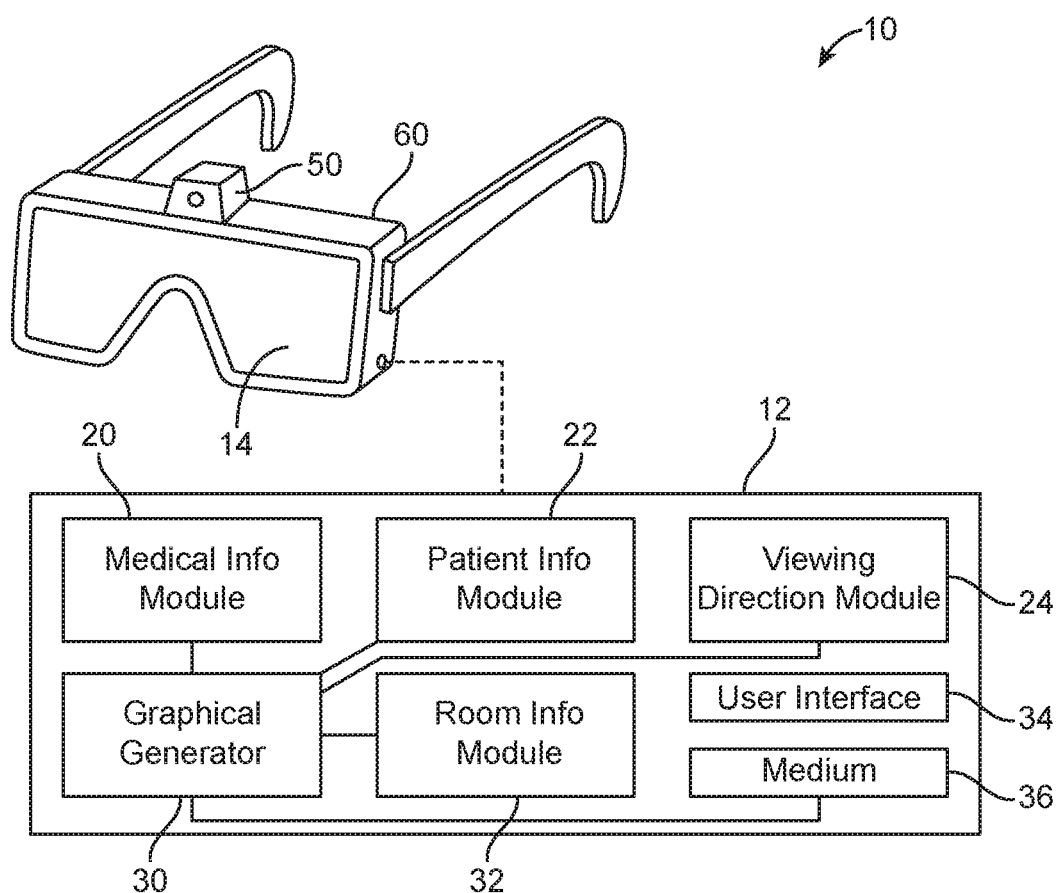
FIG. 1 illustrates an apparatus for use in a medical process.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates an apparatus 10 for use in a medical process. The apparatus 10 includes a processing unit 12 and a screen 14 configured for displaying a graphical representation of medical information for a user of the apparatus 10. The processing unit 12 is configured to obtain medical information, obtain a viewing direction of the user of the apparatus, and process the medical information based on the viewing direction of the user of the apparatus 10 to create the graphical representation of the medical information for presentation to the user of the apparatus 10.

As shown in the figure, the processing unit 12 of the apparatus 10 includes a medical information module 20 configured to obtain medical information, a patient information module 22 configured to obtain patient information, and a viewing direction module 24 configured to obtain a viewing direction of the user of the apparatus 10. The processing unit 12 also includes a graphics generator 30 coupled to the medical information module 20, the patient information module 22, and the viewing direction module. The graphics generator 30 is configured to receive the medical information from the medical information module 20, receive the patient information from the patient information module 22, and the viewing direction from the viewing direction module 24, and create the graphical representation of the medical information for display on the screen 14 of the apparatus 10 for viewing by the user of the apparatus 10.

In the illustrated embodiments, the processing unit 12 also optionally includes a room information module 32 configured to obtain room information. In some cases, the processing unit 12 may create the graphical representation of the medical information also based on the room information from the room information module 32.

The processing unit 12 may also optionally include a user interface 34 configured to receive user input from the user of the apparatus 10. The user interface 34 may be configured to allow a user to enter a command, such as a selection of the type of medical information for display on the screen 14, the format of the graphical representation of the medical information, etc. The user interface 34 may also be configured to receive input from the user for controlling a medical device, such as a treatment planning device, a treatment device, an imaging device, a patient support, or any combination of the foregoing.

The processing unit 12 may also optionally include a non-transitory medium 36 for storing data. The data may be medical information obtained by the medical information module 20, patient information obtained by the patient information module 22, viewing direction obtained by the viewing direction module 24, room information obtained by the room information module 32, or any combination of the foregoing. Also, the data stored in the non-transitory medium may be information derived from the patient information, from the room information, from the viewing direction, or any combination of the foregoing. In some embodiments, the non-transitory medium 36 may also store a treatment plan for a particular patient, and patient identity information for a particular patient.

As shown in FIG. 1, the apparatus 10 is in a form of a wearable device that includes the screen 14, and a frame 60 to which the screen 14 is secured. In some embodiments, the screen 14 may be transparent (e.g., at least partially transparent) for allowing the user of the apparatus 10 to see the real world (e.g., surrounding environment). The screen 14 may be configured to display the graphics from the graphics generator 30 so that the graphics are superimposed with real objects as directly viewed by the user. Alternatively, the wearable device may be a virtual-reality device. In such cases, the screen 14 is not transparent, and is configured to provide electronic images for viewing by the user. The images may represent the environment around the user, and may be displayed in real-time. Accordingly, the images presented by the electronic screen 14 may change in real time in accordance with a viewing direction of the user.

In other embodiments, the screen 14 may be a part of a holographic device configured to project three-dimensional images in a field of view of the user in real-time.

In further embodiments, the screen 14 may be a part of a handheld device. By means of non-limiting examples, the handheld device may be a cell phone (e.g., an IPHONE), an IPAD, an IPAD MINI, a tablet, etc.

In some embodiments, the apparatus 10 includes an orientation sensor coupled to the wearable device. For example, the orientation sensor may include one or more accelerometer(s). In such cases, the processing unit 12 may be configured to vary the graphical representation displayed on the screen 14 based on an input from the orientation sensor. For example, as the user of the apparatus 10 tilts or turns his/her head, the processing unit 12 will correspondingly vary the graphics on the screen 14 to match the viewing orientation of the user. Also, in some embodiments, the apparatus 10 includes a positioning device coupled to the wearable device. The positioning device is configured to determine a position of the apparatus 10 with respect to some defined coordinate. The positioning device may use active signals or passive signals to generate positional information regarding a position of the apparatus 10. The processing unit 12 is configured to vary the graphical representation displayed on the screen 14 based on an input from the positioning device. For example, if a user moves further away from the patient, the processing unit 12 will correspondingly vary the graphics (e.g., reduce the size of the graphics) on the screen 14 to match the viewing distance. In further embodiments, the apparatus 10 may include both an orientation sensor and a positioning device. In such cases, the graphical representation displayed on the screen 14 has a variable configuration that corresponds with the viewing direction and viewing distance of the user.

In some embodiments, in addition to the medical information, the processing unit 12 is configured to obtain patient information regarding a geometry of a patient. In such cases, the processing unit 12 may be configured to process the medical information based on both (1) the patient information and (2) the viewing direction of the user of the apparatus 10. By means of non-limiting examples, the patient information may be an image of a person (such as, a digital image of the patient, a digital image of another person different from the patient, or a model of an artificial patient), a size of the patient, a shape of the patient, etc. In some cases, the processing unit 12 may be configured to generate a graphics based on the medical information, and transmit the graphics for display on the screen 14 in a superimposed configuration with respect to the image of the person. In other cases, the patient information may be information regarding a geometry of the patient, and the processing unit 12 may be configured to generate the graphics representing the medical information based on the patient geometry. In one implementation, patient information may be obtained using one or more camera(s). The camera(s) may be optical camera(s), and/or time-of-flight camera(s) configured to provide distance information. The camera(s) may be attached or implemented at the apparatus 10. Alternatively, the camera(s) may be secured to another object (e.g., a wall, a ceiling, a floor, a patient support, a part of a treatment device, etc.) located in a treatment room. In further embodiments, a camera may be attached or implemented at the apparatus 10, while another camera may be secured to another object in the treatment room. In the embodiment in which the camera is a time-of-flight camera, the camera may provide information regarding a surface of the patient that is based on the distance information. In such cases, the output from the camera may be used by the processing unit 12 to generate the surface of the patient, or a model representing a surface of the patient.

In other embodiments, the patient information itself may be considered as an example of medical information.

In further embodiments, the medical information may comprise planned dose, delivered dose, image of internal tissue of a patient, target shape, target position, critical organ shape, critical organ position, or any combination of the foregoing. The processing unit 12 is configured to provide a graphics representing such medical information for display on the screen 14, so that the graphics appears in an overlay configuration with respect to the patient, or with respect to an image (e.g., a real-time image) of the patient.

In some embodiments in which the medical information comprises dose information, the processing unit 12 may be configured to create the graphical representation of the dose information based on the viewing direction of the user, and to provide the graphical representation for display over a patient or for display in an overlay configuration with an image of the patient.

Also, in some embodiments, the medical information may comprise tissue geometry (e.g., tissue size, shape, etc.). In such cases, the processing unit 12 may be configured to create the graphical representation of the tissue geometry based on the viewing direction of the user, and to provide the graphical representation for display over a patient or for display in an overlay configuration with an image (e.g., a real-time image) of the patient.

In one or more of the embodiments described herein, the processing unit 12 may be configured to create the graphical representation of the medical information along one or more isocenter axes as viewed by the user. Alternatively, the processing unit 12 may be configured to create the graphical representation of the medical information along a direction that is orthogonal to the viewing direction of the user of the apparatus 10. In further embodiments, the orientation of the graphics representing the medical information may be user-prescribed. In one implementation, the apparatus 10 may include a user interface (e.g., with one or more buttons and/or controls) for allowing the user of the apparatus 10 to select a direction of the cross section of an organ or tissue for display on the screen 14 in an overlay configuration with respect to the patient or with respect to an image (e.g., real-time image) of the patient. For example, if the user wants to see a certain cross section of the liver of the patient while the patient is supported on the patient support, the user may use the user interface of the apparatus 10 to prescribe such cross section with the desired orientation. In such cases, the processing unit 12 will process the user input and derive the cross section based on a CT image of the patient. In some embodiments, the user interface of the apparatus 10 may also allow the user to select which organ or tissue to display on the screen 14.

In other embodiments, the user interface may also allow the user of the apparatus 10 to determine a treatment parameter for a treatment plan while a patient is supported on a patient support. By means of non-limiting examples, the treatment parameter may be a target position to which treatment energy is to be delivered, a critical organ position at which treatment energy is to be limited or avoided, a collision-free zone for protecting the patient (i.e., components of the treatment system cannot move within such collision-free zone), etc.

In addition, in some embodiments, the processing unit 12 may be configured to obtain a CT image of a patient as an example of patient information, and the medical information may be dose information. In such cases, the processing unit 12 may be configured to obtain the medical information by calculating the dose information based on the CT image. For example, one or more anatomical features obtained from the CT image may be utilized in the determination of dose information. The processing unit 12 then generates a graphics representing the dose information for display on the screen 14 of the apparatus 10.

In further embodiments, the processing unit 12 may be configured to obtain a patient model created based on a detected surface of the patient. The detected surface may be obtained using output from one or more time-of-flight cameras (e.g., depth cameras). In such cases, the processing unit 12 may be configured to process the medical information based on the patient model and the viewing direction of the user of the apparatus 10 to create the graphical representation for display on the screen 14 of the apparatus 10. In some cases, the patient model may comprise a volumetric model approximating a shape of the patient and densities within the patient. In one specific example, the patient model may be a CT image, or a cross section of a CT image.

In further embodiments, the medical information may comprise dose information. In such cases, the processing unit 12 may be configured to determine the dose information based on the patient model. For example, the patient model may be used by the process unit 12 to determine certain fiducial point(s) of the patient. The fiducial point(s) establishes certain position and orientation of the patient. Based on the position and orientation of the patient, the processing unit 12 may then create a graphics representing dose information so that the dose information will be aligned with the correct part of the patient (or the correct part of the image of the patient) when the dose information is displayed on the screen 14.

In other embodiments, the medical information may comprise a depth of a treatment isocenter. In such cases, the processing unit 12 may be configured to render the depth of the treatment isocenter over a patient (e.g., with respect to a viewing direction of the user of the apparatus 10), or for display in an overlay configuration with an image (e.g., a real-time image) of the patient.

In some embodiments, the processing unit 12 may also be configured to obtain patient information. For example, the patient information may comprise a position of a patient. Also, the processing unit 12 may obtain image data of the patient as another example of the medical information. In such cases, the processing unit 12 may be configured to create the graphical representation of the image data based on the viewing direction of the user and the position of the patient. The image data may be CT image, ultrasound image, PET image, SPECT image, PET-CT image, MRI image, x-ray image, etc. In some embodiments, if the image data is a CT image, the graphical representation provided by the processing unit 12 may comprise a cross section of a CT image. In one implementation, the processing unit 12 may be configured to create the cross section of the CT image along isocenter axes. Alternatively, the processing unit 12 may be configured to create the cross section of the CT image along a direction that is orthogonal to the viewing direction of the user of the apparatus 10. In some cases, the medical information may also comprise dose information. In such cases, the graphical representation provided by the processing unit 12 may illustrate the dose information on the cross section of the CT image.

Patient Identification

In some embodiments, the processing unit 12 may be configured to provide a photograph of a patient for display on the screen 14. This allows the user of the apparatus 10 to verify an identity of the patient by comparing the photograph as it appears on the screen 14 and the patient as directly viewed by the user (if the screen is transparent).

In some embodiments, the apparatus 10 may optionally further include a sensor configured to sense a characteristic of a patient for biometric identification. By means of non-limiting examples, the characteristic may be a facial feature, an iris feature, a retina feature, a hand feature, an ear feature, a fingerprint, a voice, etc. Accordingly, the sensor may be a facial feature detector, an iris feature detector, a retina feature detector, a hand feature detector, an ear feature detector, a fingerprint detector, a microphone, etc. In one implementation, the sensor may be implemented using one or more camera(s). The sensor may be fixedly attached to, or implemented at, the apparatus 10. Alternatively, the sensor may be communicatively coupled to a component of the apparatus 10. For example, the sensor may be communicatively coupled to the frame 60 via a cable or via a wireless transceiver. The processing unit 12 is configured to receive the sensed characteristic from the sensor, and may include a comparator configured to compare the sensed characteristic with a pre-determined characteristic of the patient. If the sensed characteristic matches with the pre-determined characteristic, then the processing unit 12 may generate a signal to inform the user of the apparatus 10 that the identity of the patient is confirmed. The signal may be an audio signal, a visual signal, or both. On the other hand, if the sensed characteristic does not match with the pre-determined characteristic, then the processing unit 12 may generate a signal to inform the user of the apparatus 10 that the identity of the patient is not confirmed. Such signal may be an audio signal, a visual signal, or both.

In further embodiments, the apparatus 10 may also optionally include an identification sensor configured to sense an identification of a patient. By means of non-limiting examples, the identification sensor may be a barcode sensor configured to sense (e.g., read) a barcode, a quick-response (QR) sensor configured to obtain a QR response, a RFID sensor configured to sense an ID using radiofrequency, etc. The identification sensor may be fixedly attached to, or implemented at, the apparatus 10. Alternatively, the identification sensor may be communicatively coupled to a component of the apparatus 10. For example, the identification sensor may be communicatively coupled to the frame 60 via a cable or via a wireless transceiver. The processing unit 12 may processed the sensed identification and output it for display on the screen 14. The processing unit 12 may also be configured to receive the sensed identification from the identification sensor, and may include a comparator configured to compare the sensed identification with a pre-determined identification of the patient. If the sensed identification matches with the pre-determined identification, then the processing unit 12 may generate a signal to inform the user of the apparatus 10 that the identification of the patient is confirmed. The signal may be an audio signal, a visual signal, or both. On the other hand, if the sensed identification does not match with the pre-determined identification, then the processing unit 12 may generate a signal to inform the user of the apparatus 10 that the identification of the patient is not confirmed. Such signal may be an audio signal, a visual signal, or both.

It should be noted that the apparatus 10 is not limited to using the above patient information for identifying the patient or for assisting the identification of the patient. In other embodiments, the apparatus 10 may use other types of patient information. For examples, in other embodiments, the processing unit 12 may provide information regarding an age of the patient, a diagnose of the patient, a treatment site for the patient, name, identification, etc. for display on the screen 14 of the apparatus 10. The user of the apparatus 10 may utilize such patient information to confirm that the patient on the patient support is the intended patient.

In further embodiments, the apparatus may include a microphone for receiving a sound from the patient. The processing unit 12 may perform voice recognition (e.g., via a voice recognition module) to see if the received voice matches with that for the intended patient. If so, the processing unit 12 may generate an indicator to inform the user that the patient identification is correct.

In other embodiments, the apparatus may include an eye-feature detector for detecting a feature of the eye of the patient. The processing unit 12 may perform eye recognition (e.g., via an eye recognition module) to see if the detected eye feature matches with that for the intended patient. If so, the processing unit 12 may generate an indicator to inform the user that the patient identification is correct.

Other Patient Information

It should be noted that the processing unit 12 is not limited to providing the above patient information for display on the screen 14 of the apparatus 10. The processing unit 12 may also provide other patient information for display on the screen 14. By means of non-limiting examples, the processing unit 12 may provide information to indicate disease information of the patient, existing pre-conditions of the patient, future appointment(s) of the patient, warnings (e.g., blood sample results that may prevent treatment), insurance for the patient, billing status, etc. As another example of patient information, the processing unit 12 may also provide patient workflow information—e.g., treatment planning task, treatment task, imaging task, diagnostic tasks, etc., for the patient. As a further example of patient information, the processing unit 12 may also provide questions for the user of the apparatus 10 to ask the patient while the patient is supported on the patient support.

As other examples of patient information, the processing unit 12 may also provide an image (two-dimensional image or a three-dimensional image) of a target in the patient for display on the screen 14. In the embodiment in which the screen 14 has a see-through region for allowing the user to view the patient directly, the image of the target may be displayed on the screen 14 so that when the user views the patient through the screen 14, the image of the target appears over the patient. Such feature allows the user of the apparatus 10 to perform patient positioning. In other cases, instead of, or in addition to, image of the target, the processing may provide a body outline of the patient, and/or image(s) (e.g., two-dimensional image(s) or three-dimensional image(s)) of target from treatment simulation(s) or from previous treatment(s), for display on the screen 14. These information may also be helpful in assisting the user of the apparatus 10 to perform patient positioning.

In another example of patient information, the processing unit 12 may provide an image of virtual tattoo(s) for display on the screen 14. The virtual tattoo(s) has predetermined position(s) with respect to the patient, and may be used by the user of the apparatus 10 to perform patient positioning.

In some cases, to assist the user of the apparatus 10 in performing patient positioning, the processing unit 12 may also provide virtual lasers for display on the screen 14. In the embodiment in which the screen 14 has a see-through region for allowing the user to view the patient directly, the virtual lasers may be displayed on the screen 14 so that when the user views the patient through the screen 14, the image of the virtual lasers will appear over, or extending inside, the patient.

The processing unit 12 may also provide other positioning aids for display on the screen 14 to assist the user of the apparatus 10 in performing patient setup. For example, the processing unit 12 may provide graphics for allowing the user to visualize a side of the patient/patient support/fixation device/treatment device that may be obstructed by treatment device or other object(s). As another example, the processing unit 12 may provide image(s) of implant(s) in the patient for display in the screen 14 so that the implant(s) image(s) will appear over the patient (when the user view the patient directly through the transparent region of the screen 14) in correspondence with the actual position(s) of the implant(s). By means of non-limiting examples, the implant(s) may be radiopaque marker(s), active transmitter(s), passive transmitter(s), gold seed(s), etc.

As other examples of patient information, the processing unit 12 may be configured to obtain information regarding a pacemaker in the patient, electrocardiogram (ECG) for the patient, electromyography (EMG) for the patient, positioning signals for the patient, or any combination of the foregoing. The processing unit 12 may provide such information for display on the screen 14 of the apparatus. In some cases, the positioning signals may be signals output from one or more implants, such as Calypso implants. The information regarding the pacemaker may be a position of the pacemaker, and/or signals and timing of signals of the pacemaker. The information regarding ECG may be a position of the ECG device, and/or signals and timing of signals of the ECG. The information regarding the EMG for the patient may be a position of the EMG device, and/or data provided by the EMG device. The information regarding positioning signals for the patient may be a position of the device providing the positioning signals (e.g., position of an implant), and/or the positioning signals.

Workflow Assistance Information

Also, in some embodiments, the processing unit 12 may be configured to provide workflow assistance information for display on the screen 14 to assist the user of the apparatus 10 to perform treatment setup. By means of non-limiting examples, the workflow assistance information may include tasks checklist, timer for the next treatment, remaining time for next appointment, etc. Also, in some cases, the workflow assistance information may be identification of object(s) in the treatment room that need to be operated on (e.g., for setup).

Room Information

In some embodiments, the processing unit 12 is further configured to obtain room information, and to generate positional information based on the room information for assisting the user of the apparatus 10 to position a patient. In such cases, the processing unit 12 may be configured to provide the positional information for display on the screen 14.

In some cases, the room information may comprise a position of an object in a room. By means of non-limiting examples, the object may be a component of a machine, a patient support, a wall, a floor, a ceiling, an alignment device, etc.

Also, in some embodiments, the positional information generated based on the room information may be a three-dimensional position of the object in the room with respect to certain coordinate (e.g., a coordinate of the apparatus 10). In one implementation, the positional information may be generated by the processing unit 12 based on a transformation that convert the position of the object in the room in a first coordinate system to the position in a second coordinate system.

In other embodiments, the positional information may be a desired (expected) position of the patient with respect to the position of the object in the room. In such cases, the processing unit 12 may be configured to determine the desired (expected) position of the patient with respect to the position of the object in the room, and provide the desired position as the positional information for display on the screen 14.

In further embodiments, the positional information may be an actual position of the patient with respect to the position of the object in the room. In such cases, the processing unit 12 may be configured to determine the actual position of the patient with respect to the position of the object in the room, and provide the actual position of the patient as the positional information for display on the screen 14.

Also, in some cases, the medical information may be an actual position of a patient. In such cases, the processing unit 12 may be configured to provide the graphical representation of the actual position of the patient for display on the screen 14. The processing unit 12 may also provide a graphical representation of the desired position of the patient for display on the screen 14, so that the user of the apparatus 10 can see the difference between the actual position and the desired position of the patient. In other embodiments, the medical information may be a desired position of the patient.

In some embodiments, the screen 14 is configured to display the graphical representation of the expected position and/or the actual position of the patient in a field of view of the user while the user is viewing the patient in real-time. Accordingly, as the user moves around to change the field of view, the expected position and/or the actual position of the patient as displayed on the screen 14 is updated in real-time.

In some embodiments, the apparatus 10 may further include a user interface for allowing the user to position the patient based on the graphical representation of the expected position of the patient. For example, based on the actual position of the patient and the expected position of the patient, the user interface may be operated by the user to move the patient so that the actual position of the patient is aligned with the expected position of the patient. In one implementation, the user interface may control a position of a patient support so that movement of the patient may be achieved by movement of the patient support supporting the patient.

In other embodiments, the processing unit 12 may be configured to obtain room information for device validation. For example, the apparatus 10 may include a detector (e.g., a camera, a marker detector, an identifier detector, etc.) for detecting the presence of one or more objects in the treatment room. The object may be a treatment machine, a patient support, a fixation device (e.g., a face mask, a harness, etc.) for fixing a portion of the patient in place, a bolus, a medication, an accessory, etc. In some cases, the processing unit 12 may be configured to determine an outline of an object, and perform shape analysis to determine if the object matches an object that is expected to be used during treatment (e.g., an object prescribed in the treatment plan). If the object matches the prescribed object, then the processing unit 12 may generate a message for display on the screen 14 to inform the user that the detected object in the treatment room is validated. Also, in some embodiments, the processing unit 12 may provide virtual objects for display on the screen 14 to inform the user that those objects need to be provided in the treatment room. The user may then look for those objects to confirm that they are presence and to validate the objects. The virtual objects may be photographs of the objects, three-dimensional models of the objects, three-dimensional photographs of the objects, or identifiers of the objects.

Collision Avoidance

In some embodiments, the apparatus 10 may also optionally include an object sensor for sensing a patient, and object(s) next to the patient. In one implementation, the object sensor may be a depth sensing camera, such as a TOF camera. In other embodiments, the object sensor may be other types of sensor, such as a surface detector, etc. The processing unit 12 is configured to receive distance information from the object sensor, and determine surfaces of objects based on the distance information. The processing unit 12 may also be configured to identify the objects based on the determined surfaces. Also, in some embodiments, the processing unit 12 may be configured to generate a signal for notifying the user of the apparatus 10 in response to a sensed object being within a certain distance from a surface of the patient. For example, a safety zone may be determined to be 4 inches above the surface of the patient. In such cases, the processing unit 12 may determine a surface model having a surface that is 4 inches offset from the surface of the patient. During treatment, the processing unit 12 may be configured to continuously detect the objects around the patient in real-time. If an object is detected to be within the safety zone, then the processing unit 12 may generate a warning signal (e.g., an audio signal, a visual signal, or both) to inform the user of the apparatus 10. The processing unit 12 may also generate a control signal to stop an operation of a medical device, such as a treatment device that is being used to treat the patient.

In some embodiments, the graphics generator 30 may be configured to generate graphics representing one or more detected objects around the patient. The object may be a gantry, an energy source, a portal imager, a patient support, a fixation device (e.g., a mask, a harness, etc.) for maintaining a part of the patient stationary with respect to another object, etc. The graphics may be displayed on the screen 14 for viewing by the user of the apparatus 10.

In some embodiments, if the apparatus is a wearable device, the object sensor may be fixedly attached to the wearable device. In other embodiments, the object sensor may be fixedly attached to a treatment machine, a patient support, an imaging device, or any object in a treatment room (such as a floor, a wall, a ceiling, etc.). In such cases, the object sensor may be communicatively coupled to the wearable device via a cable or a wireless transmitter.

In one implementation, the processing unit 12 may include a collision prevention module configured to prevent collision between the patient and surrounding object(s), and/or between two or more objects. For example, the collision prevention module may be configured to monitor devices surrounding the patient, and generate a warning signal if two objects are within a certain prescribed distance. In some cases, the collision prevention module may be configured to monitor a moving gantry and a patient support to prevent these two devices from colliding. In other cases, the collision prevention module may be configured to monitor an imager (e.g., a kV imager) and a positioning device (e.g., Calypso console) located next to the patient to prevent these two devices from colliding.

Also, in some embodiments, the processing unit 12 may be configured to generate a collision-free envelope for display on the screen 14 of the apparatus 10. The collision-free envelope may be generated based on positions of the various objects detected in the treatment room. For example, the apparatus 10 may include a camera, or any of other types of sensing device, for detecting the treatment machine. The processing unit 12 may be configured to determine the position of the treatment machine, as well as the position(s) of one or more components associated with the treatment machine, such as the position of a moveable radiation source. Based on a degree of freedom and/or designed movement path of the radiation source, the processing unit 12 determines a three dimensional space in which the radiation source may be placed. The processing unit 12 may determine corresponding three dimensional space for other objects in the treatment room. By assembling all of these three dimensional spaces in which positions of the various objects are possible, the processing unit 12 can then determine a collision-free space in which none of the objects (other than the patient) can be placed. In some embodiments, the processing unit 12 may be configured to provide graphics for display on the screen 14 so that the colliding parts of the various items (e.g., patient, patient support, fixation device, treatment machine, etc.) can be visualized by the user of the apparatus 10. In addition, in some embodiments, the processing unit 12 may be configured to provide a graphic indicating a collision free zone for display on the screen 14 for assisting the user of the apparatus 10 to position the patient. In some cases, the collision free zone may be determined by the processing unit 12 by determining a collision-free space that the objects around the patient cannot be moved to. Such collision-free space may then be used as the collision free zone for display on the screen 14. Alternatively, the processing unit 12 may provide a safety of margin by reducing such collision-free space further to obtain a reduced collision-free space. The reduced collision-free space may then be used as the collision free zone for display on the screen 14.

Furthermore, in some embodiments, the processing unit 12 may be configured to perform a virtual dry-run by simulating movements of the various objects in the treatment room. The simulated movements may be based on the actual condition (e.g., position, shape, etc.) of the objects as detected in the treatment room. For example, the simulated movement of the object may be conducted so that the movement path begins at, or intersects with, the actual position of the object. The processing unit 12 may also provide graphics indicating the simulated movements of the objects for display on the screen 14 of the apparatus 10. For example, the processing unit 12 may provide a video showing how an object moves relative to the patient. In the embodiment in which the screen 14 of the apparatus 10 has a see-through region for allowing the user to view the patient directly, the video may be presented directly over the patient as seen by the user. This way, the user can visualize how the movement of an object will impact the patient. Also, in some cases, the virtual dry-run may also include a simulation of energy delivery. For example, simulated doses from different energy delivery directions may be tracked and accumulated at target region to determine a simulated dose effect on the target region and/or at critical organ next to the target region.

Figure 2A:
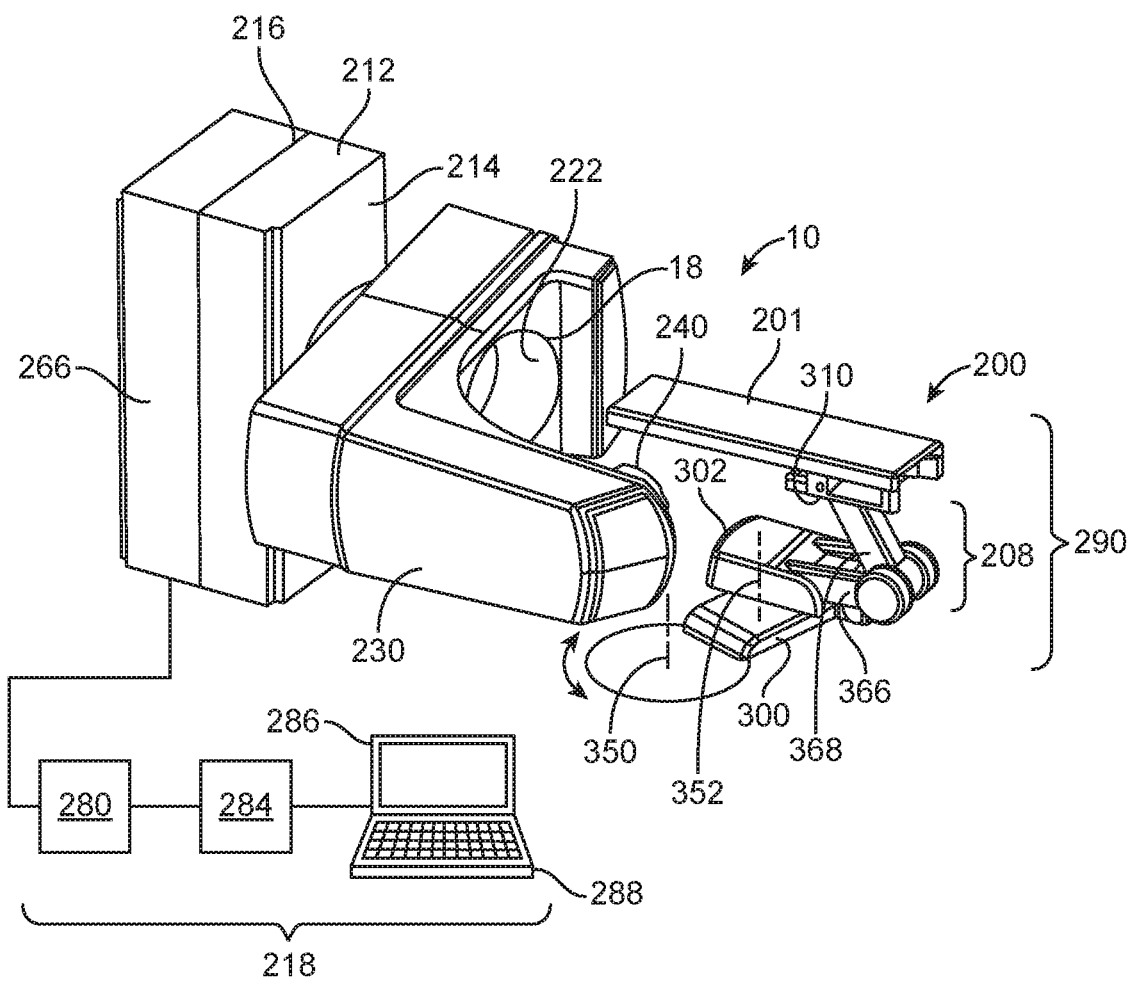
FIG. 2A illustrates a treatment system with which the apparatus of FIG. 1 can be used.

FIG. 2A illustrates a treatment system being used with the apparatus of FIG. 1. The radiation system 200 includes a structure 212 having a first side 214, and a second side 216. In the illustrated embodiments, the structure 212 has a through bore sized for accommodating at least a part of a patient. The through bore of the structure 212 provides a passage for allowing at least a portion of a patient to be transported from one side of the structure 212 to an opposite side of the structure 212. In some embodiments, a diagnostic procedure (e.g., an imaging procedure) is performed on the patient on one side of the structure 212 (e.g., for the purpose of obtaining information, such as a position of a target region, of the patient), and the patient is then transported through the bore to the opposite side of the structure 212 for a treatment procedure. In other embodiments, the patient is treated on one side of the structure 212, and is then transported through the bore to the opposite side of the structure 212 for further procedure(s), such as a diagnostic procedure (e.g., to evaluate a treatment procedure, or to verify location, orientation, and/or shape of a target tissue) or a treatment procedure.

It should be noted that the shape and configuration of the structure 212 should not be limited to the example discussed previously, and that the structure 212 can have other configurations in other embodiments. For example, in other embodiments, the structure 212 can have a curvilinear shape, or other shapes. Also, in some embodiments, the structure 212 can have a size and shape such that the structure can house mechanical and electrical components associated with an operation of the radiation system 200 as desired. The radiation system 200 also includes a radiation source 240 (located closer to the first side 214 than the second side 216) for delivering a radiation beam. The radiation beam can be a pencil beam, a fan beam, a cone beam, or other types of beams having different configurations. As used in this specification, the term "radiation source" refers to an emission point/region of a radiation beam (e.g., radiation beam), and may or may not include components, such as a particle generator, an accelerator, a cooling system, a shielding, etc., that are used to generate the radiation beam. As shown in the figure, the radiation system 200 includes an arm 230 secured to the structure 212, and the first radiation source 240 is secured to the arm 230. Some or all of the components used to generate the radiation beam can be housed within the arm 230, the structure 212, a separate housing (not shown), or combination thereof. For example, in some embodiments, the accelerator associated with the radiation source 240 may be housed within the arm 230. In such cases, one or more magnets (electromagnet(s) or permanent magnet(s)) may be provided within the arm 230 for changing a characteristic (e.g., a trajectory) of an electron beam created by the accelerator. If permanent magnet(s) is used, its associated magnetic field can be trimmed electromagnetically (e.g., using one or more electromagnetic coil(s)) or mechanically (e.g., using one or more permanent magnet(s)). Also, in some embodiments, the mechanical trimming can be performed using a magnetic shunt.

In other embodiments, or any of the embodiments described herein, the radiation system 200 may not include the arm 230. In such cases, the first radiation source 240 may be rotatably secured to the structure 212. For example, the radiation source 240 may be secured to a ring (which may be a full ring or a partial ring) that is rotatable relative to the structure 212 in a slip-ring configuration. In such cases, at least some of the components within arm 230 may be disposed within the structure 212.

In the illustrated embodiments, the radiation source 240 is a treatment radiation source for providing treatment energy. In such cases, the radiation system 200 further includes one or more collimators (not shown) for controlling a delivery of the radiation beam (e.g., changing a shape of the beam). A collimator can be, for example, a multi-leaf collimator, which is known in the art. Alternatively, the radiation source 240 can be a diagnostic radiation source for providing diagnostic energy. In some embodiments, the treatment energy is generally those energies of 160 keV or greater, and more typically 1 MeV or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. For example, a radiation beam having an energy level that is typically used for treatment purpose may be considered as having a diagnostic energy level if the radiation beam is used for diagnostic purpose (e.g., for imaging). As such, the term "treatment energy" and the term "diagnostic energy" should not be limited to energy levels having certain magnitudes. In further embodiments, the radiation source 240 is a multi-energy x-ray source that is capable of providing radiation energy at different energy levels. By way of example, the radiation source 240 is able to generate X-ray radiation at a plurality of photon energy levels within a range anywhere between approximately 10 kilo-electron-volts (keV) and approximately 20 mega-electron-volts (MeV). Radiation sources capable of generating X-ray radiation at different energy levels are described in U.S. Pat. No. 6,888,919, entitled "RADIOTHERAPY APPARATUS EQUIPPED WITH AN ARTICULABLE GANTRY FOR POSITIONING AN IMAGING UNIT," issued on May 3, 2005, and U.S. Pat. No. 7,649,981, entitled "MULTI-ENERGY X-RAY SOURCE," issued on Jan. 19, 2010, both of which are expressly incorporated by reference in their entirety.

In the illustrated embodiments, the radiation system 200 further includes a control system 278. The control system 278 includes a processor 284, such as a computer processor, coupled to a control 280. The control system 278 may also include a monitor 286 for displaying data and an input device 288, such as a keyboard or a mouse, for inputting data. In some embodiments, during an operation of the radiation system 200, the radiation source 240 rotates about the patient (e.g., as in an arc-therapy). The rotation and the operation of the radiation source 240 are controlled by the control 280, which provides power and timing signals to the radiation source 240 and controls a rotational speed and position of the radiation source 240 based on signals received from the processor 284. Although the control 280 is shown as a separate component from the structure 212 and the processor 284, in alternative embodiments, the control 280 can be a part of the structure 212 or the processor 284.

In any of the embodiments described herein, the radiation system 200 can further include an imager located next to the first opening 218 and opposite from the radiation source 240. Such imager may be configured to function as an on-board imager during a treatment procedure.

It should be noted that the radiation system 200 should not be limited to the configuration discussed previously, and that the radiation system 200 can have other configurations in other embodiments.

As shown in FIG. 2A, the radiation system 200 further includes a patient support system 290 for supporting and positioning the patient. The patient support system 290 includes a base 300 rotatably coupled to a floor so that the base 300 is ratatable about a vertical axis 350. The patient support system 290 also includes a support structure 302 rotatably coupled to the base 300 so that the support structure 302 is rotatable relative to the base 300 about another vertical axis 352. The patient support system 290 also includes an arm system 208 having a first arm 366 and a second arm 368. The arm system 208 is coupled to the support structure 302 and a patient support 201. The arms 366, 368 are configured to move in correspondence with respect to each other to change an elevation of the patient support 201. The patient support system 290 further includes a positioner 310 configured to translate the patient support 201 along a longitudinal axis of the patient support 201.

During a treatment procedure, the patient support system 290 can position the patient in various degrees of freedom. For example, the patient support system 290 can be operated to rotate the patient about the axis 350 and/or the axis 352 to place the patient at different co-planar positions with respect to the treatment machine. The patient support system 290 can also varies the height or elevation of the patient in synchronization with a position of the radiation source 240. Also, the patient support system 290 can translate the patient horizontally to move the patient to an operative position associated with the radiation source 240. The patient support system 290 can also translate the patient horizontally to move the patient into an opening 222 at the arm 230, and through a bore at the structure 212 to reach an operative position associated with another medical device 266 on the second side 216 of the structure 212. The medical device 266 may be an imaging device (such as a CT device, a MRI device, a x-ray device, etc.), or a treatment device.

In some embodiments, the radiation system 200 can further include a x-ray source 251 and an imager 252 secured to the arm 230 (FIG. 2B), wherein the x-ray tube 251 and the imager 252 are positioned to image at least a portion of the patient. The x-ray tube 251 and the imager 252 can be used to generate data regarding a patient while the patient is positioned in an operative position associated with the radiation source 240. For example, in some embodiments, the x-ray tube 251 generates a cone beam, and the imager 252 generates cone beam CT data, which represent image of a portion of a patient. Alternatively, the imaging devices can be used for radiography or fluoroscopic imaging. In some embodiments in which the radiation system 200 does not include the arm 230, but includes a ring gantry instead, the x-ray tube 251 and the imager 252 could be attached to the ring gantry.

Figure 2B:
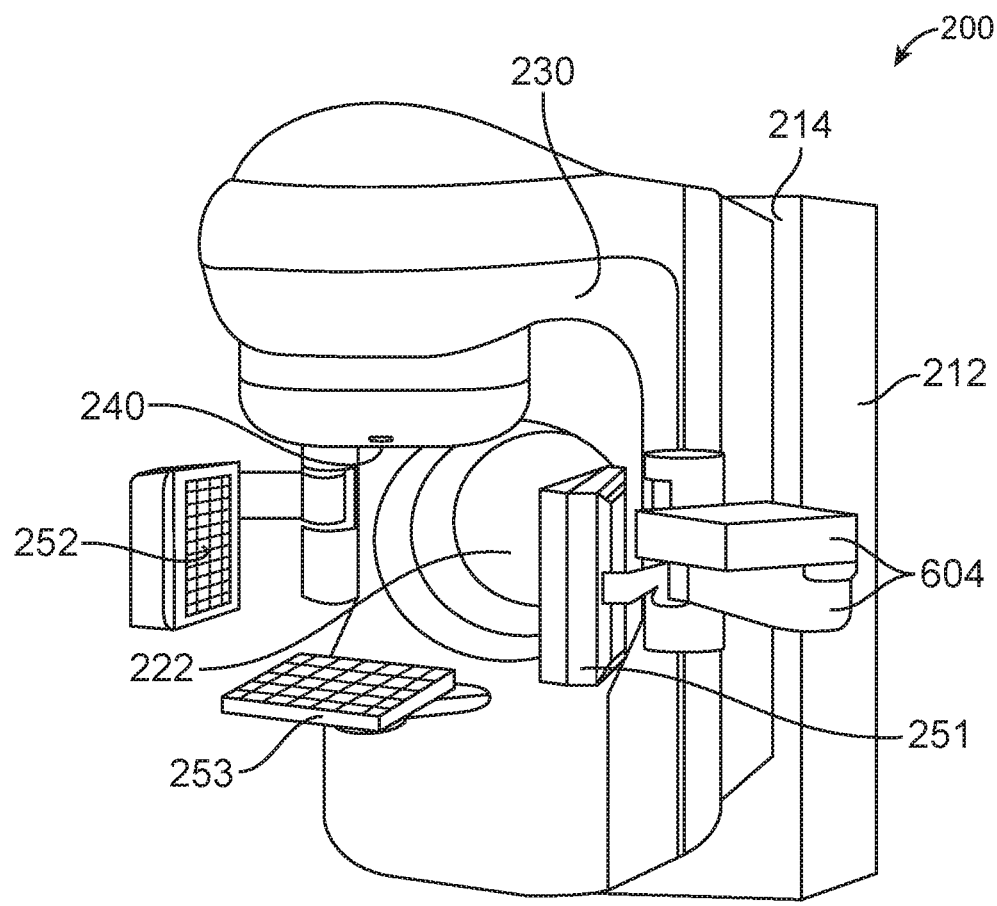
FIG. 2B illustrates another treatment system with which the apparatus of FIG. 1 can be used.

As shown in FIG. 2B, the radiation system 200 can further include an imager 253 located opposite from the radiation source 240. Such imager 253 may be configured to function as an on-board imager during a treatment procedure.

Figure 3A:
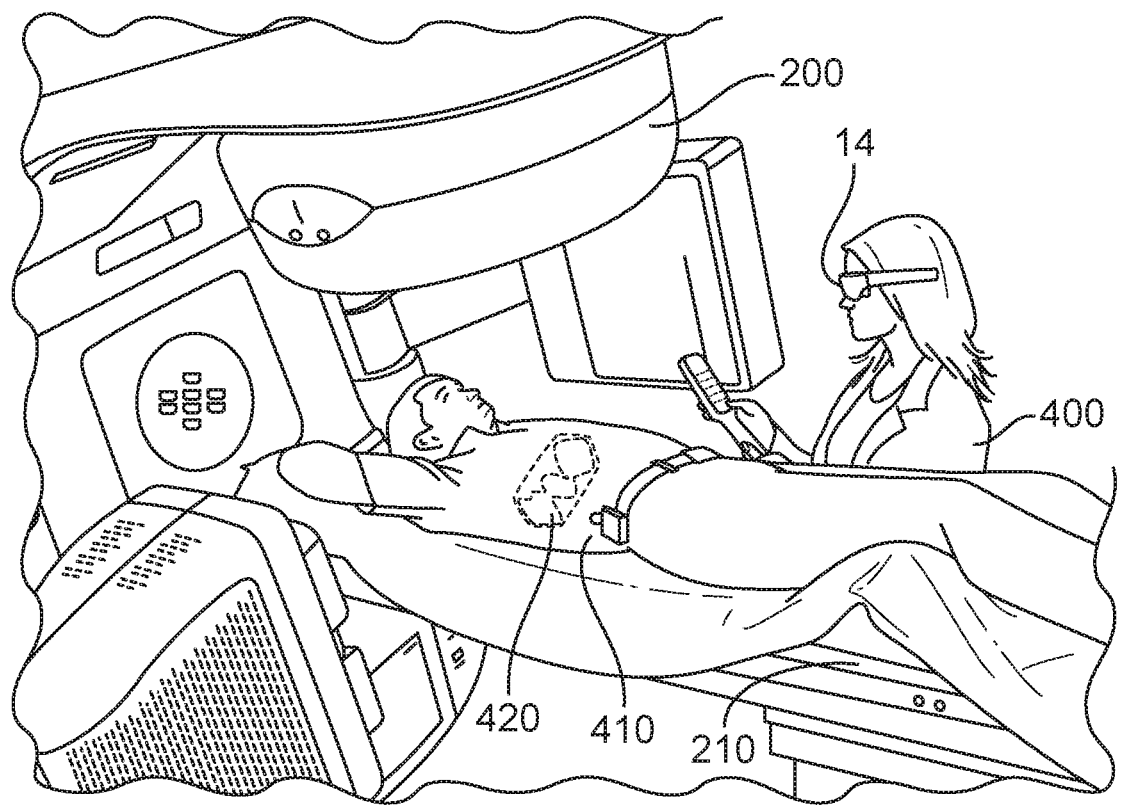
FIG. 3A-3B illustrate an example of the apparatus providing a graphical representation of medical information in an overlay configuration with respect to a patient or an image of the patient.
Figure 3B:
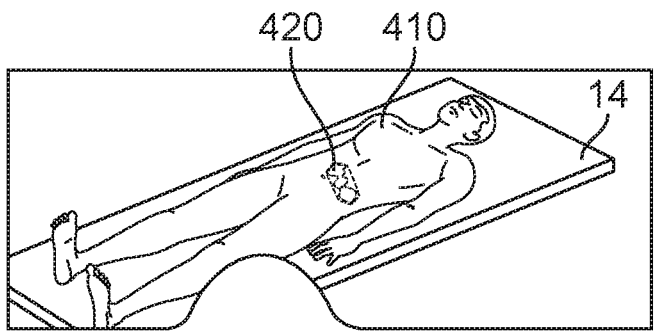

FIGS. 3A-3B illustrate an example of the apparatus 10 providing a graphical representation of medical information in an overlay configuration with respect to a patient or an image (e.g., a real-time image) of the patient, while the patient is positioned next to a treatment device. In the illustrated example, the treatment device is the radiation system 200 of FIG. 2B. However, in other embodiments, the treatment device may be any of other medical treatment devices. As shown in FIG. 3A, the user 400 is wearing the apparatus 10. The user 400 can see the patient 410 while the patient 410 is being supported on the patient support 201 next to the radiation system 200. The user 410 can also see other objects surrounding the patient 410 via the apparatus 10.

In some embodiments, the screen 14 is transparent, and so the user can see the patient 410 directly through the transparent screen 14. In other embodiments, the screen 14 may be a digital display that is a part of a virtual-reality device. In such cases, the user cannot view through the screen 14 to see the real-world. Instead, the graphics generator 30 may provide images of the patient 410 continuously in real-time. In some cases, the images of the patient 410 may be generated based on signals transmitted from an optical device (e.g., a camera).

Also, as shown in FIG. 3A and FIG. 3B, the user 400 can see medical information 420 as provided by the screen 14 of the apparatus 10. In the illustrated example, the medical information 420 is dose (e.g., delivered dose, predicted dose, and/or planned dose). In such cases, the graphics generator 30 provides a graphical representation of the dose for display on the screen 14, so that when the user view through the screen 14 to see the patient 410, the dose graphics appears in an overlay configuration with respect to the patient 410. As the user 400 moves his/her head to change the viewing direction, the graphical representation of the dose as appeared on the screen 14 will also change correspondingly (e.g., in response to the variable viewing direction of the user 400). For example, as the user 400 changes the viewing direction to view another part of the patient 410, the graphics generator 30 will correspondingly change the medical information so that the user can see the dose information for the other part of the patient 410. In other cases, the user 400 can view the same part of the patient, but from a different viewing direction. In such cases, the graphical representation of the dose as appeared on the screen 14 will also change correspondingly.

In some embodiments, the dose image as rendered and displayed on the screen 14 of the apparatus 10 may be configurable based on user's preference or selection. For example, a user may use a user interface (e.g., which may be implemented at the apparatus 10, such as one or more buttons at the goggle) to select a direction of rendering for the dose image. In some cases, the user may instruct the processing unit 12 of the apparatus 10 to render the dose image in a direction that is along one or more isocenter axes. In other cases, the user may instruct the processing unit 12 of the apparatus 10 to render the dose image in a direction that is perpendicular to a viewing direction of the user.

Figure 3C:
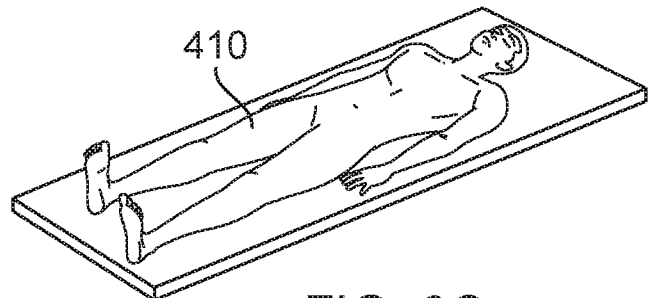
FIG. 3C illustrates what the user will see without the benefit of the apparatus of FIG. 3A.

As can be seen from the above example, the apparatus 10 is advantageous because it allows the user 400 to see medical information 420 in an overlay configuration with respect to the patient in real-time. This can occur when the user 400 is setting up the patient, reviewing delivered dose after a treatment delivery, setting up the treatment machine for a next treatment delivery, reviewing a treatment plan, and/or adjusting the treatment plan. Without the apparatus 10, the user 400 can only see the patient 410, and there is no medical information available for the user 400 to view while the user is looking at the patient 410 (FIG. 3C).

In the example shown in FIG. 3A, there is only one user 400 wearing the apparatus 10. In other embodiments, there may be multiple users 400 wearing corresponding apparatuses 10.

In the above example, the dose information may be considered to be an example of medical information. In other example, the medical information may be image data of the patient. By means of non-limiting examples, the image data may be CT image, digital x-ray image, ultrasound image, MRI image, PET image, PET-CT image, SPECT image, SPECT-CT image, etc.

Figure 4A:
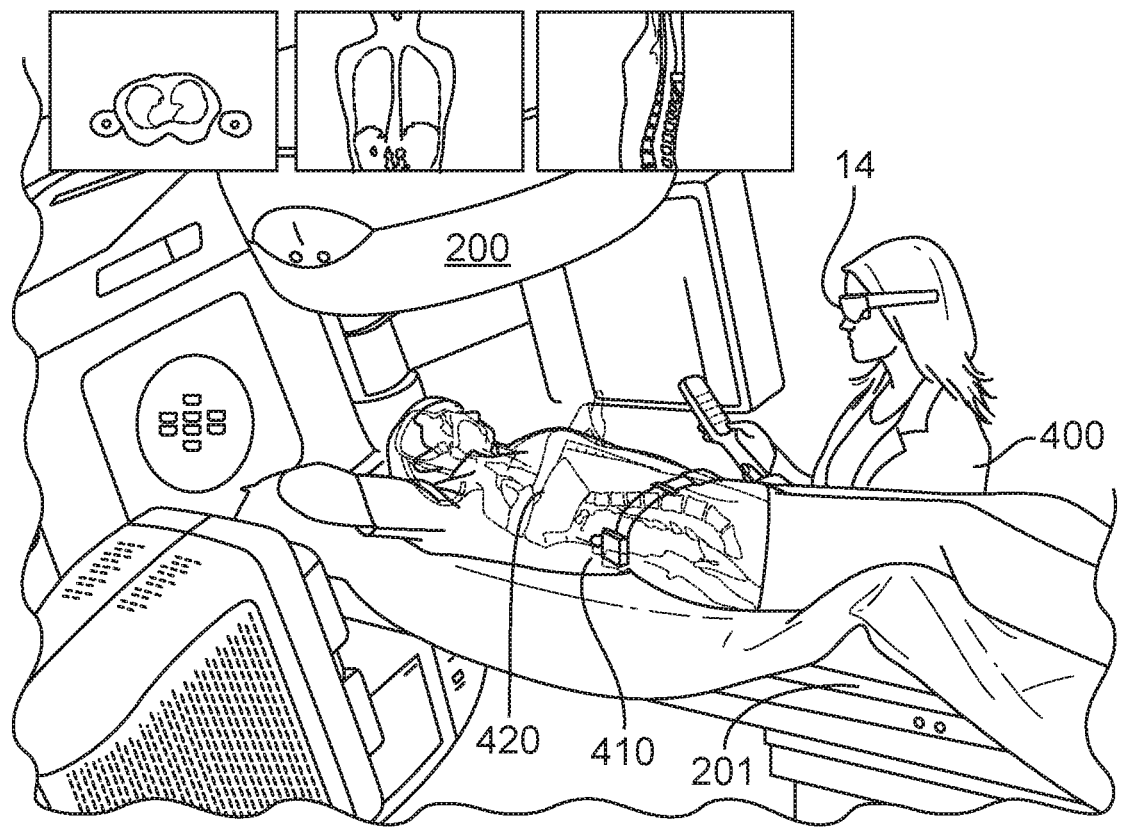
FIGS. 4A-4B illustrates another example of the apparatus providing a graphical representation of medical information in an overlay configuration with respect to a patient or an image of the patient.
Figure 4B:
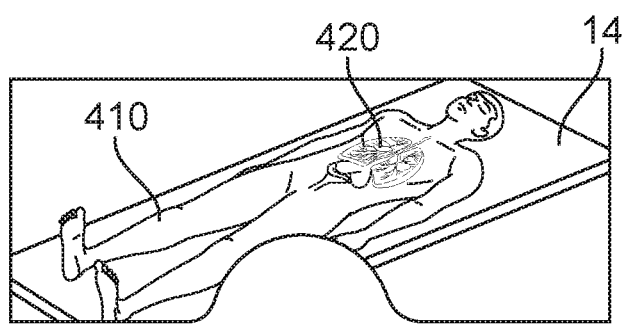

FIGS. 4A-4B illustrates another example of the apparatus 10 providing a graphical representation of medical information in an overlay configuration with respect to a patient or an image (e.g., a real-time image) of the patient, while the patient is positioned next to a treatment device. In the illustrated example, the treatment device is the radiation system 200 of FIG. 2B. However, in other embodiments, the treatment device may be any of other medical treatment devices. As shown in FIG. 4A, the user 400 is wearing the apparatus 10. The user 400 can see the patient 410 while the patient 410 is being supported on the patient support 201 next to the radiation system 200. The user 410 can also see other objects surrounding the patient 410 via the apparatus 10.

Also, as shown in FIG. 4A and FIG. 4B, the user 400 can see medical information 420 as provided by the screen 14 of the apparatus 10. In the illustrated example, the medical information 420 is internal image (CT image) of the patient 410. In such cases, the graphics generator 30 provides the internal image for display on the screen 14, so that when the user view through the screen 14 to see the patient 410, the internal image appears in an overlay configuration with respect to the patient 410. As the user 400 moves his/her head to change the viewing direction, the internal image as appeared on the screen 14 will also change correspondingly (e.g., in response to the variable viewing direction of the user 400). For example, as the user 400 changes the viewing direction to view another part of the patient 410, the graphics generator 30 will correspondingly change the medical information so that the user can see the internal image for the other part of the patient 410. In other cases, the user 400 can view the same part of the patient, but from a different viewing direction. In such cases, the internal image of the patient 410 as appeared on the screen 14 will also change correspondingly.

In some embodiments, the CT image as rendered and displayed on the screen 14 of the apparatus 10 may be configurable based on user's preference or selection. For example, a user may user a user interface (e.g., which may be implemented at the apparatus 10, such as one or more buttons at the goggle) to select a direction of rendering for the CT image. In some cases, the user may instruct the processing unit 12 of the apparatus 10 to render the CT image in a direction that is along one or more isocenter axes. In other cases, the user may instruct the processing unit 12 of the apparatus 10 to render the CT image in a direction that is perpendicular to a viewing direction of the user. Also, the user may instruct the processing unit 12 to provide surface rendering, which shows organ surfaces. In other cases, the user may instruct the processing unit 12 to provide cross sectional view of the internal organs of the patient 410.

In the above example, the medical information is image data that comprises CT image. In other embodiments, the image data may be digital x-ray image, ultrasound image, MRI image, PET image, PET-CT image, SPECT image, SPECT-CT image, etc.

Figure 4C:
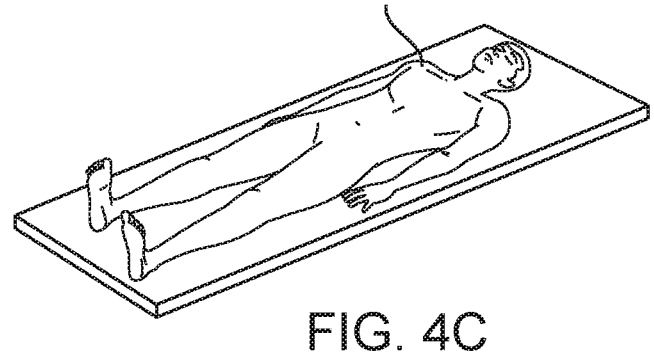
FIG. 4C illustrates what the user will see without the benefit of the apparatus of FIG. 4A.

As can be seen from the above example, the apparatus 10 is advantageous because it allows the user 400 to see medical information 420 in an overlay configuration with respect to the patient in real-time. This can occur when the user 400 is setting up the patient, reviewing delivered dose after a treatment delivery, setting up the treatment machine for a next treatment delivery, reviewing a treatment plan, and/or adjusting the treatment plan. Without the apparatus 10, the user 400 can only see the patient 410, and there is no medical information available for the user 400 to view while the user is looking at the patient 410 (FIG. 4C).

In the example shown in FIG. 4A, there is only one user 400 wearing the apparatus 10. In other embodiments, there may be multiple users 400 wearing corresponding apparatuses 10.

In one or more embodiments described herein, the processing unit 12 is configured to align the graphics as displayed on the screen 14 with a certain part of the patient, or with a certain part of an image of the patient. This way, as the user of the apparatus 10 changes his/her viewing direction, the graphics will change in real-time and will remain aligned with the correct part of the patient or the correct part of the image of the patient. In one implementation, the apparatus 10 may be configured to detect certain part(s) of the patient in real-time. Such may be accomplished using one or more cameras to view the patient. Images from the camera(s) may then be processed by the processing unit 12 to determine the position(s) of certain part(s) of the patient. In some cases, markers may be placed at the patient to facilitate the accomplishment of such purpose. In other cases, anatomical landmarks at the patient may be utilized as markers. In other embodiments, the camera(s) may be depth camera(s) for detecting the surface of the patient. The detected surface may then be utilized by the processing unit 12 to identify the position of the patient (e.g., position(s) of certain part(s) of the patient). Once the actual position of the certain part(s) of the patient has been determined, the processing unit 12 then determines a position of the graphics (representing certain medical information) with respect to the determined actual position. The position of the graphics may then be utilized by the processing unit 12 for correct positioning of the graphics at the right location of the screen 14. For example, if the medical information comprises an image of an internal part of the patient, the position of the internal part of the patient with respect to certain part P of the patient is known, or may be derived from analysis of the image. During use of the apparatus 10, the processing unit 12 analyzes real-time images of the patient to determine the actual position of the same part P of the patient. Based on the known relative positioning between the image of the internal part of the patient and the certain part P of the patient, then processing unit 12 then places the graphics (representing the same internal part of the patient) at the same relative position with respect to the actual position of the certain part P of the patient at the screen 14 in real-time.

Figure 5:
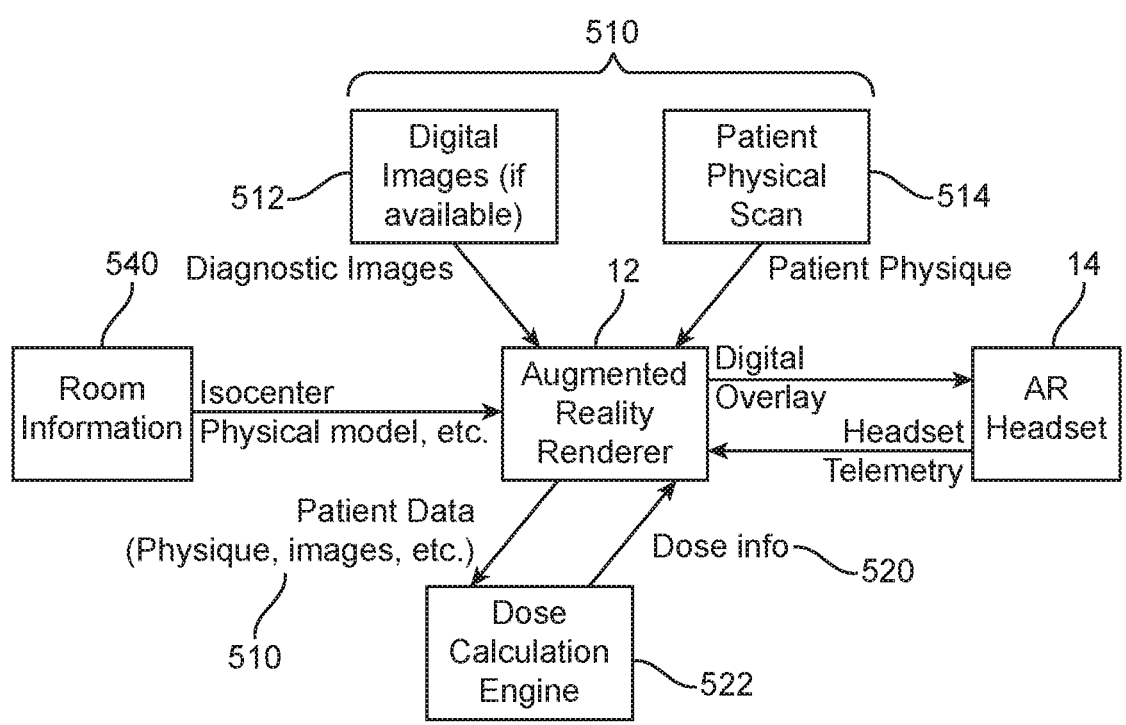
FIG. 5 illustrates information flow for the apparatus of FIG. 1.

FIG. 5 illustrates information flow for the apparatus of FIG. 1. As shown in the figure, the processing unit 12 of the apparatus 10 may receive various information, and may be configured to process such information for display at the screen 14 of the apparatus 10. In particular, the processing unit 12 may have one or more input(s) for receiving patient information 510, such as diagnostic image 512 or patient's physical scan 514. The image or the scan may be a CT image, a PET image, a x-ray, a MRI, a PET-CT, an ultrasound image, etc. Also, patient information 510 may comprise any information regarding a feature of a patient. In some cases, one or more camera(s) may be employed to obtain images of the patient, and the images are processed to obtain patient information.

The processing unit 12 may also have one or more input(s) for receiving dose information 520 (such as estimated dose, actual dose, planned dose, etc.). In one implementation, the dose information 520 may be obtained from a dose calculation engine 522. Also, patient information 510, such as images of the patient, patient's weight, patient's height, dimension, etc., may also be received from the dose calculation engine 522 in some embodiments.

The processing unit 12 may further include one or more input(s) for receiving room information 540. By means of non-limiting examples, the room information 540 may include information regarding a position of an object in a room, a physical dimension and shape of an object in a room, a model representing an object in a room, an image of an object in a room, a feature associated with an object in a room, or any combination of the foregoing, wherein the object may be a wall, a ceiling, a floor, a device in the room, etc. In some cases, the room information 540 may be isocenter location associated with the treatment machine. Also, in some embodiments, room information may comprise information regarding any feature in a room. In one implementation, one or more camera(s) may be employed to obtain images of object(s) in a room, and the images are processed to obtain the room information.

In some embodiments, the same input at the processing unit 12 may be utilized to receive multiple information, such as patient information 510 and dose information 520, or patient information 510 and room information 540, or room information 540 and dose information 520, or patient information 510, room information 540, and dose information 520.

It should be noted that the apparatus 10 is not limited to a wearable device that is in a form of goggle or glasses. In other embodiments, the apparatus 10 may be in a form of a helmet, hood, facemask, etc., that is for worn at the head of the user. In other embodiments, the apparatus 10 may be in a form of a handheld device. By means of non-limiting examples, the handheld device may be a cell phone, an iPad, a miniPad, a tablet, etc.

Figure 6:
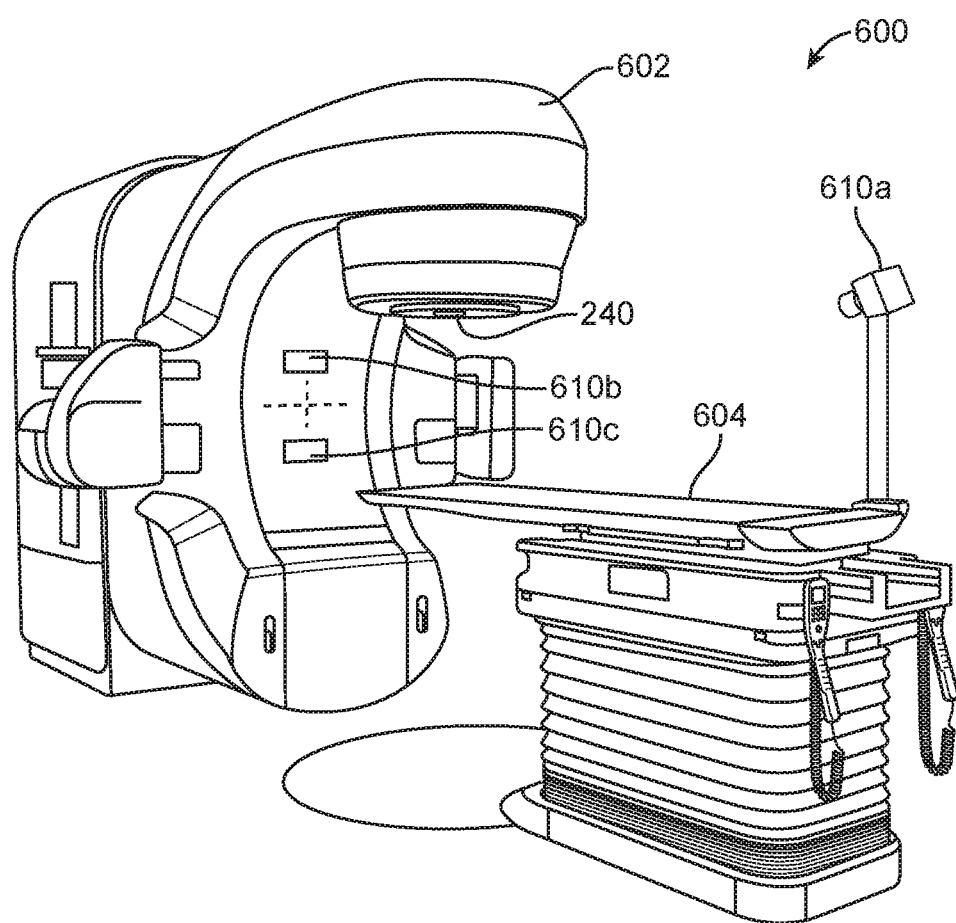
FIG. 6 illustrates a treatment system having a camera system that may be used with the apparatus of FIG. 1.

As discussed, in some embodiments, the processing unit 12 of the apparatus 10 may obtain patient information and/or room information from a camera. The camera may be fixedly secured to the apparatus 10. In other embodiments, the camera may be secured to a patient support. FIG. 6 illustrates a treatment system 600 having a camera system that may be used with the apparatus 10 of FIG. 1. As shown in the figure, the treatment system 600 includes a treatment machine 602 and a patient support 604. A camera 610*a* is secured to the patient support 604. The treatment machine 602 may be the same as that shown in FIG. 2B in some embodiments. During use, the camera 610*a* generates images of the patient supported on the patient support 604 and images of objects surrounding the patient in real time. The images are transmitted to the processing unit 12 of the apparatus 10 of FIG. 1, which processes the images to obtain patient information and/or room information. As shown in FIG. 6, in some embodiments, the treatment system 600 may also include additional cameras 610*b*, 610*c* for obtaining patient information (e.g., images of the patient) and/or room information (e.g., images of components of the treatment machine 602 in a treatment room).

In other embodiments, there may be multiple cameras. For example, the apparatus 10 may have multiple cameras that are fixedly secured to the apparatus 10. For example, if the apparatus 10 is in the form of goggle, then the cameras may be secured to a frame of the goggle. In other embodiments, there may be multiple cameras attached to different objects in a treatment room. In such cases, the cameras provide images of the objects in the treatment room in real time, and transmit the images to the processing unit 12 of the apparatus 10. In further embodiments, there may be one or more camera(s) attached to the apparatus 10, and one or more camera(s) attached to different objects in the treatment room. During use, the camera(s) at the apparatus 10 and the other camera(s) in the treatment room provide real time images to the processing unit 12, which processes the images to determine patient information and/or room information.

Figure 7:
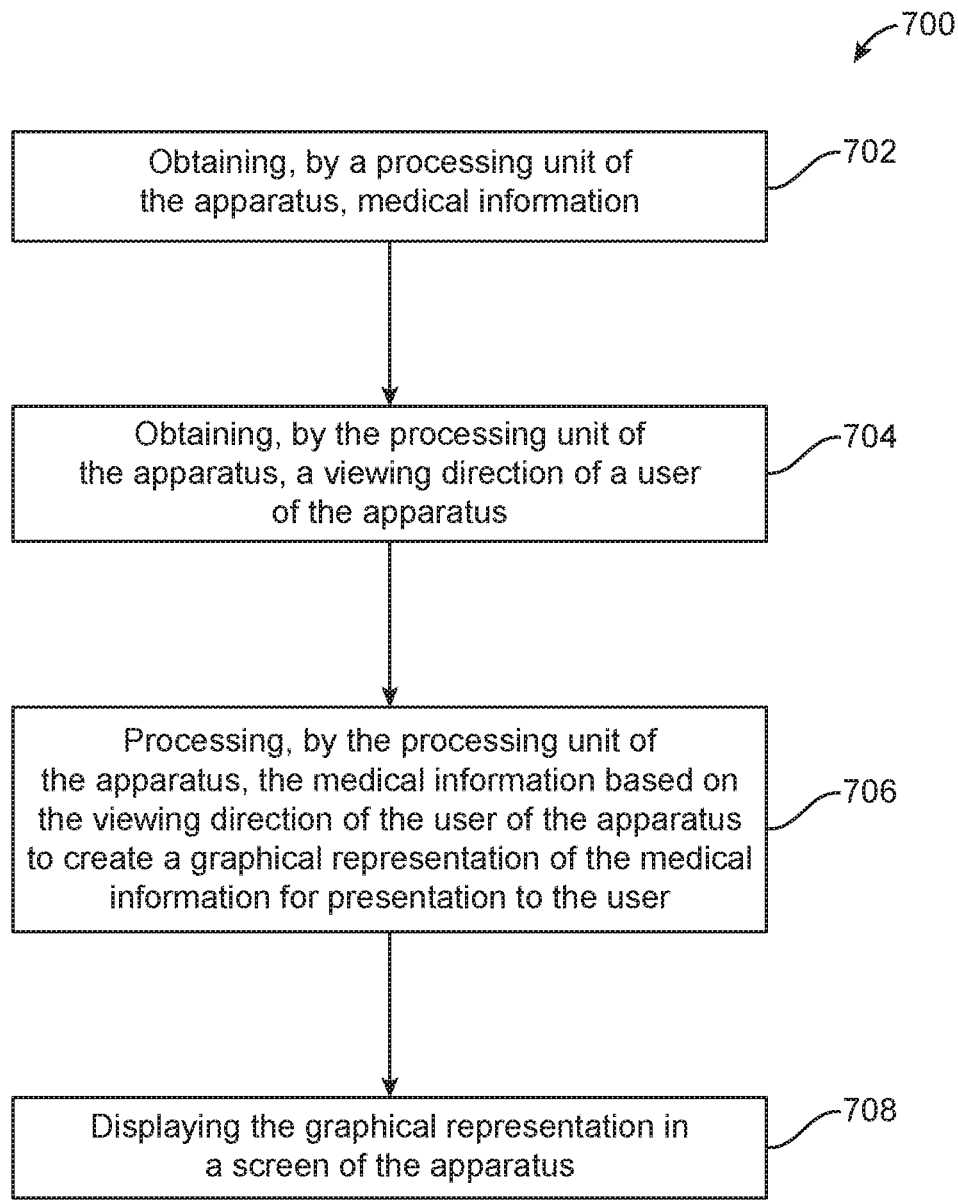
FIG. 7 illustrates a method in accordance with some embodiments.

FIG. 7 illustrates a method 700 in accordance with some embodiments. The method 700 may be performed by an apparatus, such as the apparatus 10, in a medical process. The medical process may be a treatment process and/or an imaging process. Also, the treatment process may be a radiation treatment process. In other embodiments, the treatment process may involve other types of energy that is different from radiation. By means of non-limiting examples, the treatment energy involved in the treatment process may be radiofrequency energy, thermal energy, ultrasound energy, proton energy, electron energy, etc. Also, in some embodiments, the medical process may involve a particle accelerator. For example, the medical process may be a proton treatment process, a radiation therapy, a x-ray process, a CT imaging process, etc., each of which involves use of a particle accelerator. Referring to the figure, the method 700 includes: obtaining, by a processing unit of the apparatus, medical information (item 702); obtaining, by the processing unit of the apparatus, a viewing direction of a user of the apparatus (item 704); processing, by the processing unit of the apparatus, the medical information based on the viewing direction of the user of the apparatus to create a graphical representation of the medical information for presentation to the user (item 706); and displaying the graphical representation in a screen of the apparatus (item 708). In some embodiments, the processing unit involved in items 702, 704, 706 may be the processing unit 12 of the apparatus 10. In other embodiments, the processing unit involved in items 702, 704, 706 may be any other processing unit.

In some embodiments, the act of obtaining the medical information in item 702 may be performed by the processing unit receiving the medical information from another component. In other embodiments, the act of obtaining the medical information in item 702 may be performed by the processing unit determining (e.g., deriving) the medical information based on data received by the processing unit.

Also, in some embodiments, the act of obtaining the viewing direction of the user of the apparatus in item 704 may be performed by the processing unit receiving the viewing direction from another component, such as an orientation sensor. The orientation sensor may be coupled to the same device that contains the processing unit, or may be separate from the processing unit. In other embodiments, the act of obtaining the viewing direction in item 704 may be performed by the processing unit determining the viewing direction based on data received by the processing unit.

In addition, in some embodiments, the act of processing the medical information based on the viewing direction of the user of the apparatus to create the graphical representation of the medical information in item 706 may be performed by the a graphics generator of a processing unit (e.g., the processing unit 12), which determines a configuration of the graphical representation based on the viewing direction of the user. In some embodiments, the medical information comprises image data, such as CT data. In such cases, the processing unit creates a CT image rendering based on the viewing direction, so that when the CT image rendering is displayed in a screen, the CT image rendering will correspond with a position of a patient as directly viewed by the user, or will correspond with a position of an image of the patient as viewed by the user. In some embodiments, the processing unit is configured to create the cross section of the CT image along isocenter axes. In other embodiments, the processing unit is configured to create the cross section of the CT image along a direction that is orthogonal to the viewing direction of the user.

In other embodiments, the medical information may comprise a depth of a treatment isocenter. In such cases, the depth of the treatment isocenter may be rendered by the processing unit over a patient (e.g., with respect to a viewing direction of the user of the apparatus 10), or for display in an overlay configuration with an image (e.g., a real-time image) of the patient.

In further embodiments, the medical information may be any of other information described herein. By means of non-limiting examples, the medical information may be information or data regarding a feature of a patient, an actual position of the patient, a desired position of the patient, a model of a patient, etc.

In some embodiments, the act of displaying the graphical representation in item 708 may be performed by a screen that is partially or completely transparent. Such configuration allows a user of the apparatus to directly view the real world. In other embodiments, the act of displaying the graphical representation in item 708 may be performed by a screen that is a digital display of a virtual-reality device. In one implementation, the act of displaying the graphical representation may be performed by the screen 14 of the apparatus 10.

Guidance on Treatment Plan Adaptation

In one or more embodiments described herein, the apparatus 10 may be further configured to provide guidance on treatment plan adaptation. For example, the processing unit 12 may be configured to provide guidance for display on the screen 14, wherein the guidance may assist a user of the apparatus 10 in deciding whether or not to execute radiation treatment for the patient. In one implementation, guidance information may be received by the processing unit 12 (e.g., wirelessly or via a wire or cable). The processing unit 12 of the apparatus 10 may then process the guidance information for display on the screen 14. The guidance information may be determined online or offline.

In some embodiments, a physician in a different room from the treatment room may view a real-time image of the patient while the patient is on the patient support, and evaluate the treatment configuration to determine whether to proceed with the treatment or not. If the physician determines that treatment may be proceeded, the physician may then generate a signal via an electronic user interface. The signal is then transmitted to the apparatus 10 for display on the screen 14. For example, the signal may be "Proceed with treatment". Alternatively, if the physician determines that the treatment is not to be proceeded, the physician may then user the electronic user interface to generate a signal (e.g., a signal indicating "Not to proceed with treatment"), which is then transmitted to the apparatus 10 for display on the screen 14.

In further embodiments, instead of having the physician who is in a different room from the treatment room providing input for plan adaptation, the user wearing the apparatus 10 may himself/herself determines a treatment plan, and/or determine whether to adapt a treatment plan, based on guidance information displayed on the screen 14. For example, in some cases, a current treatment plan may be loaded into the treatment device while the patient is supported on the patient support. The user of the apparatus 10 may then determine a new treatment plan (different from the current treatment plan) by selecting a pre-determined treatment plan from a plurality of pre-determined treatment plans. In one implementation, the selection may be performed based on a guidance information presented on the screen 14 of the apparatus 10. For example, there may be a first treatment plan for the patient that was generated for non-filled bladder, and a second treatment plan for the patient that was generated for filled bladder. In such example, the processing unit 12 of the apparatus 10 may output a message indicating that the patient has a filled bladder for display on the screen 14. When the user of the apparatus 10 sees the message, the user may then select the treatment plan that is designed for the patient with the filled bladder. In some embodiments, the processing unit 12 may provide the guidance information (e.g., the message indicating that the patient has a filled bladder) in response to processing of a patient note or nurse's or doctor's notes, which indicates that the patient has a filled bladder. Alternatively, the processing unit 12 may be configured to obtain a real-time image of the patient (e.g., CT image, x-ray, ultrasound image, MRI image, etc.) and analyze the image to determine whether the patient has a filled bladder or not.

In other embodiments, instead of selecting one of the pre-determined treatment plans as the new treatment plan, the user of the apparatus 10 may determine the new treatment plan by changing a parameter in the current treatment plan to obtain a different treatment plan.

It should be noted that the guidance information provided by the processing unit 12 is not necessarily based on bladder condition of the patient, and that the processing unit 12 may be configured to provide guidance information based on other parameter(s). For example, in other embodiments, dose variations may be overlayed on the patient's tumor and critical organs when displayed on the screen 14, so that the treater can adjust the patient's treatment plan accordingly. As another example, the guidance information may be any information that allows the user to identify a change to the patient's anatomy. In one implementation, the processing unit 12 may be configured to display one or more planning structures on the screen 14 so that the user of the apparatus 10 can see the planning structures in an overlay configuration with the current configuration(s) of the patient, wherein the current configuration(s) may be the actual shape and geometry of the patient as viewed through the screen 14, a constructed image of an external part of the patient, or an image of an internal part of the patient. This way, if there is a change to the patient's anatomy (e.g., due to weight loss), then user may then notice the change through viewing of the screen 14.

As a further example, the processing unit 12 may be configured to process one or more current images (e.g., real-time image(s), or image(s) obtained while the patient is on the patient support next to the treatment machine) of the patient by comparing the current image(s) with planning image(s). The processing unit 12 may provide a result of the image comparison for display on the screen 14, wherein the result may be an example of guidance information that provides guidance for treatment plan determination and/or adaptation. The image comparison may be achieved by the processing unit 12 performing image shape analysis (e.g., shape recognition and shape comparison, etc.), image analysis (e.g., image correlation), or both. If the current image(s) differ by the planning image(s) and the difference exceeds a certain threshold, the processing unit 12 may then generate a message to inform the user of the apparatus of such difference for display on the screen 14. By means of non-limiting examples, the processing unit 12 may be configured to detect difference in size of target, shape of target, position of target, size of critical organ, shape of critical organ, position of critical organ, or any combination of the foregoing, based on a comparison between current image(s) and planning image(s). The current image(s) may be CT image(s), x-ray image(s), MRI image(s), ultrasound image(s), etc. Similarly, the planning image(s) may be CT image(s), x-ray image(s), MRI image(s), ultrasound image(s), etc. In some embodiments, the current image(s) may be of the same type as the planning image(s). In other embodiments, the current image(s) may be of different type as that of the planning image(s).

In other embodiments, instead of having the processing unit 12 perform image comparison between the current image and the planning image, the processing unit 12 may simply processes the current image with the planning image for simultaneous display on the screen 14. The display of the planning image and/or the current image may be considered as an example of guidance information, which provides guidance for treatment plan determination and/or adaptation. The current image may be displayed with the planning image in an overlay configuration. This way, the user of the apparatus 10 may notice any difference between the current image and the planning image. In one implementation, the processing unit 12 may identify an area in the current image that is larger than the planning image, and may provide a first color for such area. The processing unit 12 may also identify an area in the planning image that is larger than the current image, and may provide a second color for such area.

This way, when the colored areas are displayed on the screen 14, the user of the apparatus 10 will see any changes in the size and shape of the internal organ of the patient. In some cases, both of the current image and the planning image may be displayed over the patient as viewed through the screen 14, or over an image of the patient who is being supported on the patient support, based on a viewing orientation and position of the apparatus 10.

In further embodiments, the processing unit 12 may also be configured to identify a change in a patient's posture, and/or to provide information for allowing the user of the apparatus 10 to detect a change in the patient's posture. For example, in some embodiments, the processing unit 12 may be configured to generate an image of the patient, showing the posture of the patient for the treatment plan, for display on the screen 14 of the apparatus 10. The planning posture of the patient may be displayed directly over the patient as viewed through the screen 14, or in an overlay configuration with a real-time image of the patient as displayed on the screen 14. This allows the user of the apparatus 10 to see any discrepancy between the planning posture of the patient and the current posture of the patient while the patient is being supported on the patient support next to the treatment machine. In response to the detected discrepancy, the user of the apparatus 10 may position the patient or may instruct the patient to change posture, so that the current posture of the patient will match the planning posture of the patient. In one implementation, the planning posture of the patient may be represented by a constructed image that is output by the processing unit 12 based on a viewing direction and position of the apparatus 10, wherein the constructed image may be considered as an example of guidance information, which provides guidance for treatment plan determination and/or adaptation. For example, if the user of the apparatus 14 is standing towards the right side of the patient, then the processing unit 12 will generate the image indicating the planning posture as viewed from the right side of the patient. This way, when the constructed image is displayed on the screen 14 in an overlay configuration with the patient, the planning posture can be compared with the current posture from the same viewing direction and position.

In other embodiments, the processing unit 12 may be configured to detect the discrepancy between planning posture and current posture of the patient. For example, in some cases, the processing unit 12 may compare a planning image of the patient with the current image of the patient to determine if a difference in the posture exceeds a certain threshold. If the difference exceeds the threshold, the processing unit 12 may then generate a message for display on the screen 14 to inform the user of the apparatus 10. For example, if the patient's hand is incorrectly placed (which may impact treatment beam delivery, and may lead to an incorrect dose delivery), then the message will inform the user of the apparatus 10 of such. In some cases, the message may also indicate the details of the posture difference, such as, which part of the patient is incorrectly positioned, how much (the distance) the patient part is incorrectly positioned, etc. The message provided by the processing unit 12 may be considered as an example of guidance information, which guides the user in determining a treatment plan and/or adaptation of a treatment plan. The current image of the patient may be an optical camera image, a depth image, or any other types of image that indicates a feature of an exterior part of the patient. Alternatively, or additionally, the current image may indicate an interior part of the patient. Similarly, the planning image of the patient may be an optical camera image, a depth image, a constructed part of a three-dimensional image, or any other types of image that indicates a feature of an exterior part of the patient. Alternatively, or additionally, the current image may indicate an interior part of the patient.

In further embodiments, the processing unit 12 may also generate one or more images indicating treatment beam angles and positions to be achieved, and provide such image(s) for display on the screen 14 of the apparatus 10. In the illustrated embodiments, the images indicating treatment beam angles and positions may be based on viewing orientation and position of the apparatus 10. In one implementation, the images may be one or more lines representing one or more beam trajectories for one or more respective beams to be delivered from respective gantry angle(s). Optionally, the processing unit 12 may also provide an image of a target to receive the radiation beam(s) for display on the screen 14. In some embodiments, the lines representing the beam trajectories may be displayed over the patient as seen through the screen 14, or may be displayed in an overlay configuration with a real-time image of the patient as displayed on the screen 14. This allows the user of the apparatus 10 to see if any of the lines representing the radiation beams undesirably intersects a part of the patient. For example, if a line representing the radiation beam to be delivered undesirably intersects a patient's arm, the user of the apparatus 10 may then determines that the treatment configuration is not desirable. The user may in such case select a new treatment plan, adjust a parameter of the current treatment plan to obtain a new treatment plan, or may change the posture of the patient. In the above embodiments, the images representing the beam angles and positions may be considered as an example of guidance information that guides the user to determine a treatment plan and/or to adapt a treatment plan.

It should be noted that guidance information provided by the processing unit 12 for display on the screen 14 may include any treatment plan information. This way, when the user of the apparatus 10 sees the treatment plan information on the screen 14, the user may utilize such information to determine how to adjust the patient to adapt the treatment plan, and/or may utilize such information to determine whether the treatment plan can be executed. If it is determined that the treatment plan cannot be executed, then the user may determine a new treatment plan accordingly.

The treatment plan information may be any information that is involved in the treatment of the patient. The treatment plan information may be any parameter of a treatment plan, or may be any information derived from a treatment plan. For example, in some embodiments, the treatment plan information may comprise a position of an energy source for delivering a treatment beam. In such cases, the graphical representation provided by the processing unit 12 may comprise a line representing a trajectory of the treatment beam. In another example, the treatment plan information comprises an expected configuration of a component of a treatment machine. In some cases, the expected configuration may comprise an expected position of the component (e.g., a gantry, an energy source, etc.) of the treatment machine. In another example, the treatment plan information may comprise an expected dose for an internal target of a patient. In such cases, the graphical representation provided by the processing unit 12 may indicate the expected dose graphically, and the graphical representation may be displayed over a patient as viewed through the display, or may be displayed in an overlay configuration with an image of the patient, so that the graphical representation is at a location that corresponds with a position of the internal target of the patient. In a further example, the treatment plan information comprises an expected posture of a patient. The treatment plan information may also comprise a target position, a target size, a target shape, a critical organ position, a critical organ size, a critical organ shape, or any combination of the foregoing. In another example, the treatment plan information may comprise a target fluence, and the processing unit 12 may be configured to provide the graphical representation for representing the target fluence. In another example, the treatment plan information may comprise a trajectory of a component of a treatment machine. In such cases, the graphical representation provided by the processing unit 12 may be configured to indicate the trajectory of the component of the treatment machine.

In some embodiments, the processing unit 12 may be configured to simulate a treatment based on the treatment plan information. In such cases, the graphical representation provided by the processing unit 12 for display on the screen 14 may comprise one or more images represented the simulated treatment. In some cases, the one or more images may be a sequence of images forming a video. Also, in some embodiments, each of the images in the video may be based on a viewing direction and position of the user of the apparatus 10. The simulated treatment may comprise a simulated movement of a component of a treatment machine, such as the gantry, the energy source, the patient support, etc. In some cases, the graphical representation provided by the processing unit 12 for display on the screen 14 may comprise a video showing the simulated movement of the component of the treatment machine.

Also, in some embodiments, the simulated movements may be based on the actual condition (e.g., position, shape, etc.) of the objects as detected in the treatment room. For example, the simulated movement of the object may be conducted so that the movement path begins at, or intersects with, the actual position of the object. The processing unit 12 may also provide graphics indicating the simulated movements of the objects for display on the screen 14 of the apparatus 10. For example, the processing unit 12 may provide a video showing how an object moves relative to the patient. In the embodiment in which the screen 14 of the apparatus 10 has a see-through region for allowing the user to view the patient directly, the video may be presented directly over the patient as seen by the user. This way, the user can visualize how the movement of an object will impact the patient. Also, in some cases, the processing unit 12 may perform a simulation of energy delivery. For example, simulated doses from different energy delivery directions may be tracked and accumulated at target region to determine a simulated dose effect on the target region and/or at critical organ next to the target region.

In further embodiments, the processing unit 12 may be configured to provide virtual light field for display on the screen 14 of the apparatus 10. For example, in some cases, virtual light field may be displayed to allow a user of the apparatus 10 to visualize surface fluence for a simulated treatment or for an actual treatment. The virtual light field may also allow the user to see if radiation is going where it should. As another examples, the virtual light may represent fluence painting, or may represent skin flash.

In some embodiments, the processing unit 12 may also be configured to provide information regarding fluence virtualization for display on the screen 14.

In some embodiments, the apparatus 10 further includes a user interface for allowing the user to determine a new treatment plan by selecting the new treatment plan from a plurality of pre-determined treatment plans, while a patient is supported on a patient support, or by changing a parameter of a current treatment plan, while a patient is supported on a patient support. The user interface may include an input device, such as one or more buttons, one or more switches, one or more dials, a touch screen, a trackball, a joystick, etc. In some cases, the input device may be located at a frame of a goggle, a pair of glasses, visor, headgear, etc. In other cases, the input device may be implemented on a separate unit that is communicatively coupled to the wearable structure of the apparatus 10. The separate unit may be a handheld device, or may be any device that can be placed in a pocket or be clipped to a belt or clothing. In one implementation, the separate unit may be implemented using a cell phone, such as an iPhone, a smart phone, etc.

In some embodiments, the user interface may also be configured for allowing the user to control a position of an energy source, a patient support, one or more camera(s), one or more alignment laser(s), one or more light(s), a calibration of a device, a speaker for communication with a patient, music for presentation to the patient, graphics and/or videos (e.g., game for controlling a patient's breathing or breathhold) for presentation to the patient, or any combination of the foregoing. In some cases, if breathing game is presented to the patient, the processing unit 12 may also provide the same images of the game for display on the screen 14 in synchronization with the images being presented to the patient. This way, the user of the apparatus 10 may explain the game to the patient in real time, and may visualize how the patient reacts to the game.

In some embodiments, the processing unit 12 may also be configured to determine an image of a patient, and output the image of the patient for display on the screen based on the viewing direction of the user of the apparatus. By means of non-limiting examples, the image comprises a CT image, a x-ray image, a MRI image, an ultrasound image, a tomosynthesis image, an on-line image, a dose image, etc.

In one or more embodiments, the processing unit 12 may be configured to receive a real-time consultation from a person who is different from the user of the apparatus, and provide guidance information for display on the screen for assisting the user to determine and/or to adapt a treatment plan. In one implementation, the apparatus 10 may include a communication module configured to provide communication with one or more persons outside the treatment room. Data obtained from within the treatment room may be transmitted via the communication module to the person(s) outside the treatment room. The person(s) outside the treatment room may analyze the data, and provide input for reception by the apparatus 10 in the treatment room. For example, the apparatus 10 may detect a posture of the patient in the treatment room, and may transmit the detected posture to a station outside the treatment room. A person at the station may analyze the posture to determine if it matches that prescribed in the treatment plan. If the posture does not match the prescribed posture, the person at the station may then send a message to the apparatus 10 to inform the user of the apparatus 10 that the patient's posture needs to be adjusted. The message may also indicate how to adjust the patient.

In some embodiments, the processing unit 12 may be configured to obtain information from previous treatment sessions, and provide such information for display on the screen 14 of the apparatus 10. The user may utilize such information from previous treatment sessions to determine whether to adjust a treatment plan to obtain a new treatment plan for the current treatment session. For example, the processing unit 12 may be configured to obtain multiple positions of an isocenter at different respective times, and provide a graphic indicating change(s) of the isocenter over time for display on the screen. In another example, the processing unit 12 may be configured to obtain multiple values of dose at different respective times, and provide a graphic indicating how the dose varies over time. In a further example, the processing unit 12 may be configured to provide patient setup information for display on the screen, the patient setup information indicating weight change and/or positional change, of a patient. In one implementation, outlines of the patient (e.g., while supported by the patient support) may be obtained at different times, and the weight change may be indicated by changes to the outline of the patient.

In one or more embodiments, the apparatus 10 may further include a database configured to store data documenting one or more activities that occur in a treatment room. The database may be wirelessly connected to a part of the apparatus 10, or may be in communication with the part of the apparatus via a cable. In some cases, the database may be outside the apparatus 10, e.g., in the treatment room, or in another room such as a treatment console. In one implementation, the database may be implemented using cloud technology, wherein data from the apparatus 10 may be sent to the "cloud", and the apparatus 10 may obtain data from the "cloud". In other cases, the database may be implemented using a storage device that is located within the apparatus 10. By means of non-limiting examples, the database may be configured to store data representing a treatment setup configuration, a patient setup configuration, a patient behavior, or any combination of the foregoing. In another example, the database may be configured to store data indicating how a treatment was executed. For example, the data may indicate positions of a component of a treatment machine at different respective times, and/or a timing of energy delivery. In some embodiments, the database may have a database structure that is specifically configured to store the data mentioned above. Such database structure is advantageous and is an improvement in the technology of treatment analysis because it allows an executed treatment to be "played back" so that the executed treatment can be retrospectively analyzed, and results of the treatment may be processed in association with the activities of the executed treatment.

Also, in some embodiments, the apparatus 10 may include a camera unit coupled to the processing unit 12. The camera unit may include an optical camera, a depth camera, or both the optical camera and the depth camera. The camera unit may be configured to capture various scenes in the treatment room, and may output a corresponding video. In some cases, the video may be store in the database described previously. Also, in some cases, the video may be analyzed by the processing unit 12 to derive various information, such as patient identification, patient position, patient posture, positions of various components of the treatment system, etc.

Figure 8:
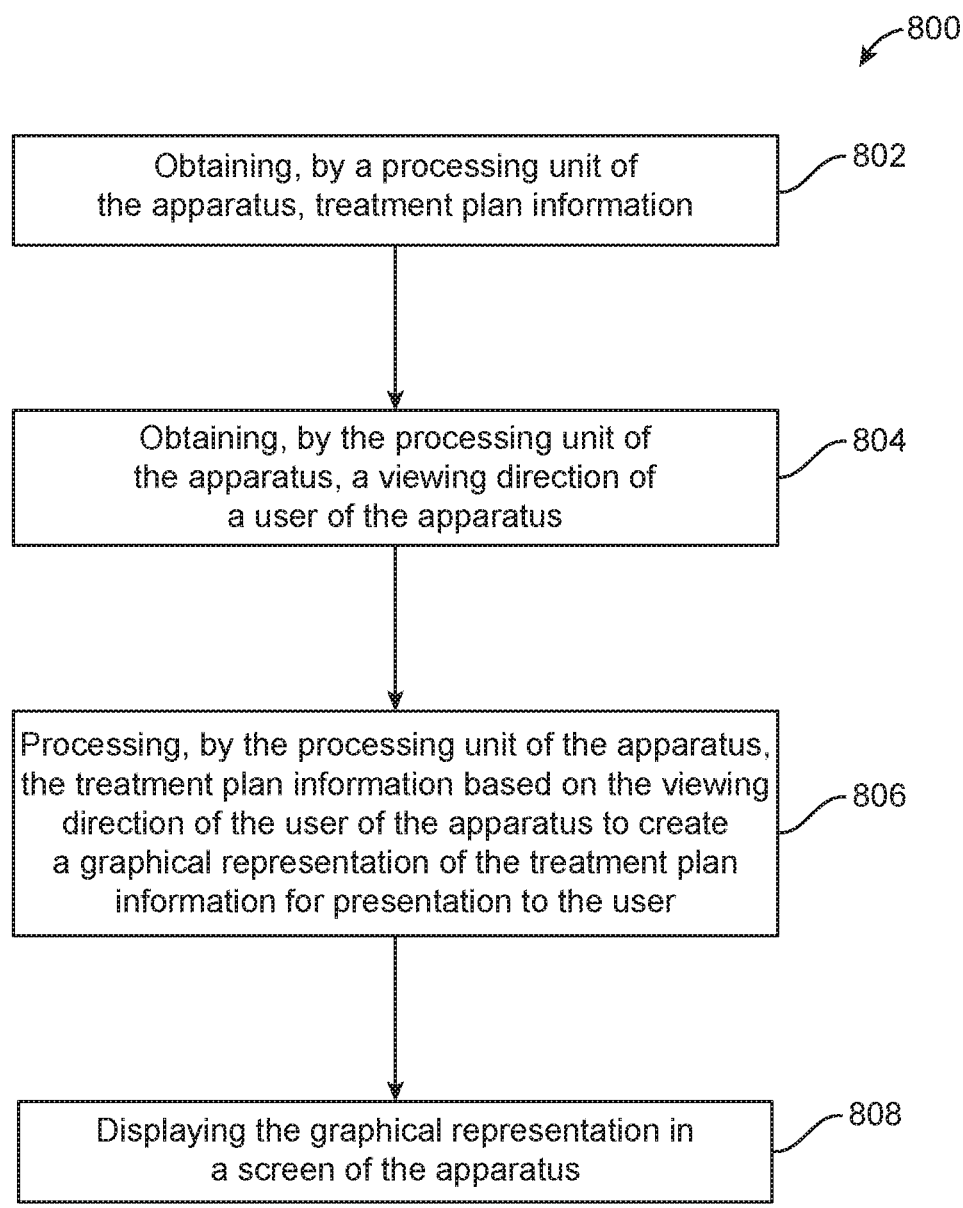
FIG. 8 illustrates another method in accordance with some embodiments.

FIG. 8 illustrates a method 800 in accordance with some embodiments. The method 800 may be performed by an apparatus, such as the apparatus 10, in a medical process. The medical process may be a treatment process. Also, the treatment process may be a radiation treatment process. In other embodiments, the treatment process may involve other types of energy that is different from radiation. By means of non-limiting examples, the treatment energy involved in the treatment process may be radiofrequency energy, thermal energy, ultrasound energy, proton energy, electron energy, etc. Also, in some embodiments, the medical process may involve a particle accelerator. For example, the medical process may be a proton treatment process, a radiation therapy, a x-ray process, a CT imaging process, etc., each of which involves use of a particle accelerator. Referring to the figure, the method 800 includes: obtaining, by a processing unit of the apparatus, treatment plan information (item 802); obtaining, by the processing unit of the apparatus, a viewing direction of a user of the apparatus (item 804); processing, by the processing unit of the apparatus, the treatment plan information based on the viewing direction of the user of the apparatus to create a graphical representation of the treatment plan information for presentation to the user (item 806); and displaying the graphical representation in a screen of the apparatus (item 708). In some embodiments, the processing unit involved in items 802, 804, 806 may be the processing unit 12 of the apparatus 10. In other embodiments, the processing unit involved in items 802, 804, 806 may be any other processing unit.

In some embodiments, the act of obtaining the treatment plan information in item 802 may be performed by the processing unit receiving the treatment plan information from another component. The treatment plan information may be considered as an example of medical information discussed previously (e.g., with reference to method 700). In other embodiments, the act of obtaining the treatment plan information in item 802 may be performed by the processing unit determining (e.g., deriving) the treatment plan information based on data received by the processing unit.

Also, in some embodiments, the act of obtaining the viewing direction of the user of the apparatus in item 804 may be performed by the processing unit receiving the viewing direction from another component, such as an orientation sensor. The orientation sensor may be coupled to the same device that contains the processing unit, or may be separate from the processing unit. In other embodiments, the act of obtaining the viewing direction in item 804 may be performed by the processing unit determining the viewing direction based on data received by the processing unit.

In addition, in some embodiments, the act of processing the treatment plan information based on the viewing direction of the user of the apparatus to create the graphical representation of the medical information in item 806 may be performed by the a graphics generator of a processing unit (e.g., the processing unit 12), which determines a configuration of the graphical representation based on the viewing direction of the user. In some embodiments, the treatment plan information comprises image data, such as CT data. In such cases, the processing unit creates a CT image rendering based on the viewing direction, so that when the CT image rendering is displayed in a screen, the CT image rendering will correspond with a position of a patient as directly viewed by the user, or will correspond with a position of an image of the patient as viewed by the user. In some embodiments, the processing unit is configured to create the cross section of the CT image along isocenter axes. In other embodiments, the processing unit is configured to create the cross section of the CT image along a direction that is orthogonal to the viewing direction of the user.

In other embodiments, the treatment plan information may comprise a depth of a treatment isocenter. In such cases, the depth of the treatment isocenter may be rendered by the processing unit over a patient (e.g., with respect to a viewing direction of the user of the apparatus 10), or for display in an overlay configuration with an image (e.g., a real-time image) of the patient.

In further embodiments, the treatment plan information may be any of other information described herein. By means of non-limiting examples, the treatment plan information may be information regarding a desired dose, a target region, a critical organ, a desired patient posture, a desired patient position, positions of energy sources, trajectory of a component of a treatment machine, etc.

In some embodiments, the act of displaying the graphical representation in item 708 may be performed by a screen that is partially or completely transparent. Such configuration allows a user of the apparatus to directly view the real world. In other embodiments, the act of displaying the graphical representation in item 808 may be performed by a screen that is a digital display of a virtual-reality device. In one implementation, the act of displaying the graphical representation may be performed by the screen 14 of the apparatus 10.

Specialized Processing System

FIG. 9 is a block diagram illustrating an embodiment of a specialized processing system 1600 that can be used to implement various embodiments described herein. For example, the processing system 1600 may be configured to provide one, some, or all of the functions of the apparatus 10 in accordance with some embodiments. Also, in some embodiments, the processing system 1600 may be used to implement the graphics generator 30, medical information module 20, room information module 32, patient information module 22, and/or the viewing direction module 24. The processing system 1600 may also be an example of any processor described herein.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus for use in a medical process that involves a particle accelerator, comprising:
   a processing unit configured to obtain three-dimensional (3D) radiation dose distribution, obtain a viewing direction of a user of the apparatus, and determine a two-dimensional (2D) graphic representing a subset of the 3D radiation dose distribution based on information in the 3D radiation dose distribution and also based on the viewing direction of the user of the apparatus for presentation to the user of the apparatus, wherein the 2D graphic representing the subset of the 3D radiation dose distribution comprises a graphical feature that corresponds with the viewing direction of the user;
   a screen for displaying the 2D graphic, wherein the screen comprises a transparent portion for allowing the user to see a patient and at least a part of a medical system;
   wherein the screen is configured to display the 2D graphic representing a subset of the 3D radiation dose distribution so that when the user views the patient through the transparent portion, the 2D graphic representing the subset of the 3D radiation dose distribution would appear over a corresponding part of the patient while the patient is in an operative position with respect to the medical system.

2. The apparatus of claim 1, further comprising a wearable device, wherein the screen is a part of the wearable device, and wherein the apparatus comprising the wearable device is configured to assist the user in setting up the patient with respect to the medical system comprising the particle accelerator.

3. The apparatus of claim 2, further comprising an orientation sensor coupled to the wearable device, wherein the processing unit is configured to change the 2D graphic representing the subset of the 3D radiation dose distribution based on an input from the orientation sensor.

4. The apparatus of claim 2, further comprising a positioning device coupled to the wearable device, wherein the processing unit is configured to change the 2D graphic representing the subset of the 3D radiation dose distribution based on an input from the positioning device.

5. The apparatus of claim 2, wherein the apparatus comprising the wearable device is configured to communicate with the medical system comprising the particle accelerator.

6. The apparatus of claim 1, wherein the processing unit is also configured to obtain patient information regarding a geometry of the patient, and process the patient information based on the viewing direction of the user of the apparatus.

7. The apparatus of claim 6, further comprising a time-of-flight camera for providing distance information, wherein the patient information comprises a surface of the patient that is based on the distance information.

8. The apparatus of claim 6, wherein the patient information comprises a digital image of the patient, a digital image of another person different from the patient, or a model of an artificial patient.

9. The apparatus of claim 1, wherein the processing unit is also configured to obtain medical information comprising one or more of: an image of internal tissue of the patient, target shape, target position, critical organ shape, or critical organ position.

10. The apparatus of claim 1, wherein the medical system comprises a treatment machine, and wherein the processing unit is configured to create the 2D graphic representing the subset of the 3D radiation dose distribution along one or more isocenter axes of the treatment machine as viewed by the user.

11. The apparatus of claim 1, wherein the processing unit is also configured to provide a user interface for allowing the user to determine a treatment parameter for a treatment plan while the patient is supported on a patient support.

12. The apparatus of claim 1, wherein the the processing unit is configured to cause the screen to display the 2D graphic together with a CT image or an image derived from the CT image.

13. The apparatus of claim 1, wherein the processing unit is also configured to obtain a patient model created based on a detected surface of the patient.

14. The apparatus of claim 13, wherein the patient model comprises a volumetric model approximating a shape of the patient and densities within the patient.

15. The apparatus of claim 14, wherein the 2D graphic representing the subset of the 3D radiation dose distribution is based on the patient model.

16. The apparatus of claim 1, wherein the processing unit is also configured to render a depth of a treatment isocenter over the patient.

17. The apparatus of claim 1, wherein the processing unit is also configured to obtain patient information, the patient information comprising a position of the patient; and
   wherein the processing unit is configured to create the 2D graphic representing the subset of the 3D radiation dose distribution based on the viewing direction of the user and the position of the patient.

18. The apparatus of claim 1, wherein comprises the processing unit is also configured to create a cross section of a CT image.

19. The apparatus of claim 18, wherein the processing unit is configured to cause the screen to display the 2D graphic representing the 3D radiation dose distribution on the cross section of the CT image.

20. The apparatus of claim 18, wherein the processing unit is configured to create the cross section of the CT image along isocenter axes.

21. The apparatus of claim 18, wherein the processing unit is configured to create the cross section of the CT image along a direction that is orthogonal to the viewing direction of the user.

22. The apparatus of claim 1, wherein the screen is a part of a holographic device.

23. The apparatus of claim 1, wherein the processing unit is also configured to provide a photograph of the patient for display on the screen.

24. The apparatus of claim 1, further comprising a sensor configured to sense a characteristic of the patient for biometric identification.

25. The apparatus of claim 24, wherein the characteristic comprises a facial feature, an iris feature, a retina feature, a hand feature, an ear feature, a fingerprint, or a voice.

26. The apparatus of claim 24, wherein the processing unit is configured to compare the sensed characteristic with a pre-determined characteristic of the patient.

27. The apparatus of claim 1, further comprising a sensor configured to sense an identification of the patient, wherein the screen is configured to display the identification of the patient.

28. The apparatus of claim 27, wherein the identification comprises a barcode, a quick-response (QR) code, or a RFID.

29. The apparatus of claim 1, wherein the processing unit is further configured to obtain room information, and to generate positional information based on the room information for assisting the user to position the patient, and wherein the processing unit is configured to provide the positional information for display on the screen.

30. The apparatus of claim 29, wherein the room information comprises a position of an object in a room, the object being a component of a machine, a patient support, a wall, a floor, a ceiling, or an alignment device.

31. The apparatus of claim 1, wherein the processing unit is configured to provide an indicator indicating an expected position of the patient for display on the screen.

32. The apparatus of claim 31, wherein the screen is configured to display the indicator of the expected position of the patient in a field of view of the user while the user is viewing the patient in real-time.

33. The apparatus of claim 31, further comprising a user interface for allowing the user to position the patient based on the indicator of the expected position of the patient.

34. The apparatus of claim 1, further comprising a sensor for sensing a component of the medical system, wherein the processing unit is configured to generate a signal for notifying the user in response to the sensed component of the medical system being within a certain distance from an exterior surface of the patient, the distance defining a safety zone around at least a part of the patient.

35. The apparatus of claim 34, wherein screen is also configured to display a safety zone that is above an exterior surface of the patient.

36. The apparatus of claim 34, wherein the sensor comprises a surface detector.

37. The apparatus of claim 1, wherein the processing unit is also configured to obtain object information regarding an object involved in the medical process, and provide the object information for display on the screen to assist in validation of an identity of the object.

38. The apparatus of claim 37, wherein the object comprises a treatment machine, a patient support, a fixation device for fixing a portion of the patient in place, a bolus, a medication, or an accessory.

39. The apparatus of claim 1, wherein the processing unit is configured to change the 2D graphic representing the subset of the 3D radiation dose distribution in real time in accordance with a change of the viewing direction.

40. The apparatus of claim 1, wherein the processing unit is configured to process the 3D radiation dose information and the viewing direction at a sufficient speed that allows the 2D graphic to be changed in real time in accordance with a change in the viewing direction.

41. The apparatus of claim 1, wherein the 3D radiation dose distribution comprises a planned 3D radiation dose distribution or a delivered 3D radiation dose distribution.

42. A method performed by an apparatus in a medical process that involves a particle accelerator, comprising:
obtaining, by a processing unit of the apparatus, three-dimensional (3D) radiation dose distribution;
obtaining, by the processing unit of the apparatus, a viewing direction of a user of the apparatus;
determining, by the processing unit of the apparatus, two-dimensional (2D) graphic representing a subset of the 3D radiation dose distribution based on information in the 3D radiation dose distribution and also based on the viewing direction of the user of the apparatus for presentation to the user, wherein the 2D graphic representing the subset of the 3D radiation dose distribution comprises a graphical feature that corresponds with the viewing direction of the user;
displaying the 2D graphic in a screen of the apparatus, wherein the screen comprises a transparent portion for allowing the user to see the patient and at least a part of a medical system comprising the particle accelerator;
wherein the 2D graphic representing the subset of the 3D radiation dose distribution is displayed in the screen so that when the user views the patient through the transparent portion, the 2D graphic representing the subset of the 3D radiation dose distribution would appear over the patient while the patient is at an operative position with respect to the medical system.

* * * * *